US010864296B2

(12) United States Patent
Lavalle et al.

(10) Patent No.: US 10,864,296 B2
(45) Date of Patent: Dec. 15, 2020

(54) POLYPEPTIDE AND HYALURONIC ACID COATINGS

(71) Applicants: INSTITUT NATIONAL DE LA SANTE ET DE LA RECHERCHE MEDICALE (INSERM), Paris (FR); Université de Strasbourg, Strasbourg (FR); PROTIP MEDICAL, Strasbourg (FR)

(72) Inventors: Philippe Lavalle, Wintzenheim (FR); Pierre Schaaf, Molsheim (FR); Nihal Engin Vrana, Strasbourg (FR); Angela Mutschler, Strasbourg (FR)

(73) Assignees: INSTITUT NATIONAL DE LA SANTE ET DE LA RECHERCHE MEDICALE (INSERM), Paris (FR); UNIVERSITÉ DE STRASBOURG, Strasbourg (FR); PROTIP MEDICAL, Strasbourg (FR)

( * ) Notice: Subject to any disclaimer, the term of this patent is extended or adjusted under 35 U.S.C. 154(b) by 0 days.

(21) Appl. No.: 15/646,684

(22) Filed: Jul. 11, 2017

(65) Prior Publication Data

US 2018/0318472 A1    Nov. 8, 2018

Related U.S. Application Data

(63) Continuation-in-part of application No. PCT/EP2017/060378, filed on May 2, 2017.

(51) Int. Cl.
| | | |
|---|---|---|
| *A61L 27/34* | (2006.01) | |
| *A61L 27/20* | (2006.01) | |
| *C08L 77/04* | (2006.01) | |
| *A61L 29/08* | (2006.01) | |
| *A61L 27/22* | (2006.01) | |
| *A61L 27/26* | (2006.01) | |
| *C08G 69/10* | (2006.01) | |
| *A01N 43/16* | (2006.01) | |
| *A01N 47/44* | (2006.01) | |
| *A61L 31/10* | (2006.01) | |
| *A61L 31/16* | (2006.01) | |
| *C09D 5/14* | (2006.01) | |
| *C09D 105/08* | (2006.01) | |
| *C09D 177/04* | (2006.01) | |
| *A61L 27/54* | (2006.01) | |

(52) U.S. Cl.
CPC .............. *A61L 27/20* (2013.01); *A01N 43/16* (2013.01); *A01N 47/44* (2013.01); *A61L 27/22* (2013.01); *A61L 27/227* (2013.01); *A61L 27/26* (2013.01); *A61L 27/34* (2013.01); *A61L 27/54* (2013.01); *A61L 29/085* (2013.01); *A61L 31/10* (2013.01); *A61L 31/16* (2013.01); *C08G 69/10* (2013.01); *C08L 77/04* (2013.01); *C09D 5/14* (2013.01); *C09D 105/08* (2013.01); *C09D 177/04* (2013.01); *A61L 2300/214* (2013.01); *A61L 2300/236* (2013.01); *A61L 2300/252* (2013.01); *A61L 2300/406* (2013.01); *A61L 2300/608* (2013.01); *A61L 2300/61* (2013.01); *A61L 2420/02* (2013.01); *A61L 2420/08* (2013.01)

(58) Field of Classification Search
CPC .......... A61L 27/34; A61L 27/54; A61L 29/16; A61L 29/085; A61L 31/10; A61L 31/16
See application file for complete search history.

(56) References Cited

U.S. PATENT DOCUMENTS

| | | | | |
|---|---|---|---|---|
| 2004/0135967 | A1* | 7/2004 | Carney | A61L 27/34 351/159.62 |
| 2006/0002974 | A1* | 1/2006 | Pacetti | A61K 31/727 424/423 |
| 2007/0154513 | A1* | 7/2007 | Atanasoska | A61F 2/91 424/423 |
| 2007/0207212 | A1* | 9/2007 | Haynie | A61K 9/167 424/490 |
| 2008/0171070 | A1* | 7/2008 | Schaaf | A61L 27/34 424/422 |

FOREIGN PATENT DOCUMENTS

WO    WO-2017/191110    11/2017

OTHER PUBLICATIONS

Mutschler, et al., "Unexpected Bactericidal Activity of Poly(arginine)/Hyaluronan Nanolayered Coatings", Oct. 31, 2016, pp. A-J, Chem. Mater.

* cited by examiner

*Primary Examiner* — Micah Paul Young
(74) *Attorney, Agent, or Firm* — B. Aaron Schulman, Esq.; Stites & Harbison, PLLC

(57) ABSTRACT

A polyelectrolyte coating comprises at least one polycationic layer consisting of at least one polyarginine as herein defined and at least one polyanionic layer consisting of hyaluronic acid. The polyelectrolyte coating has a biocidal activity and the invention thus further refers to the use of said polyelectrolyte coating for producing a device, in particular a bacteriostatic medical device, more particularly an implantable device, comprising said polyelectrolyte coating, and a method for preparing said device and a kit. Also disclosed is a method of preventing a bacterial infection in an individual.

18 Claims, 7 Drawing Sheets

POLYPEPTIDE AND HYALURONIC ACID COATINGS

CROSS-REFERENCE TO RELATED PATENT APPLICATION

This application is a continuation-in-part of PCT/EP2017/060378 filed May 2, 2017, herein incorporated by reference.

FIELD OF THE INVENTION

The present invention concerns a polyelectrolyte coating comprising at least one polycationic layer consisting of at least one polyarginine as herein defined and at least one polyanionic layer consisting of hyaluronic acid. The polyelectrolyte coating has a biocidal activity and the invention thus further refers to the use of said polyelectrolyte coating for producing a device, in particular a bacteriostatic medical device, more particularly an implantable device, comprising said polyelectrolyte coating, and a method for preparing said device and a kit. The invention further refers to a method of preventing a bacterial infection in an individual.

BACKGROUND OF THE INVENTION

Nosocomial infections (also called health care associated infections), the fourth leading cause of disease in industrialized countries, are a major health issue. Year by year, implantation of prostheses and medical devices is increasing. In the meantime the prevalence of nosocomial infections related to implants, which are reported in the literature, is constantly on the rise. It is known that half of all nosocomial infections worldwide involve a medical device. Accordingly, the most significant hospital-acquired infections, based on frequency and potential severity, are those related to procedures e.g. surgical site infections and medical devices, including urinary tract infection in catheterized patients, pneumonia in patients intubated on a ventilator and bacteremia related to intravascular catheter use.

Some key factors for the increase of medical-device related infections are i) ageing of the population, ii) multiple drug resistance bacteria, iii) poor development of new designed antibiotic molecules. In the case of medical devices like implants, the surgical site is an attractive target for pathogens and leads to early complications. To prevent such infections associated with implants, a local treatment for the first 6 hours post-implantation is of particular interest.

Innovative, bioactive, smart coatings and materials for reducing nosocomial infections are urgently needed to slow this trend.

The alternate deposition of polycations and polyanions on a substrate leads usually to the formation of a coating, called polyelectrolyte coating. Those polyelectrolyte coatings consist of a multilayered structure and their thickness increases with the number of deposition steps. The potential applications of these kinds of coatings are widespread ranging from energy storage devices to anti-fogging coatings and bioactive substrates. In this latter area, antimicrobial coatings are receiving extensive attention due to their importance in the fight against nosocomial infections.

One strategy for antimicrobial coatings consists in the design of anti-adhesive coatings to inhibit attachment and growth of pathogens on the device. These anti-adhesive coatings thus prevent biofilm formation. However, as the growth of the pathogen is not inhibited by this method, the risk of colonization of another surrounding site is high, in particular in the case of fragile and immunodeficient people.

Another strategy consists in the design of bactericidal coatings. These coatings usually release antimicrobial agents such as antibiotics that were incorporated in the coating structure either during its buildup or by diffusion in the coating after buildup. The release of the active compound can be triggered for example by enzymatic degradation of the coating or by a pH change. It can also take place naturally due to hydrolysis of one of the film constituent.

These are interesting approaches; however the release profile in situ of bactericidal coatings should be perfectly controlled to avoid negative effects of overdosed delivered drugs. Moreover, in most of the cases, the release is passive which means antimicrobial agents are delivered in the presence or absence of bacteria. To circumvent these drawbacks, contact-killing strategies could be more advantageous and consist in damaging the bacteria only when they come in contact with the surface of the material.

The inventors of the present invention have recently developed a polyelectrolyte coating using poly-L-arginine (PAR) as polycation and hyaluronic acid (HA) as polyanion. Said coating was used as a powerful surface coating with antimicrobial properties and with immunomodulatory properties (Özçelik, H. et al., 2015, Adv. Health. Mat, 4: 20126-2036). However, in this strategy, an antimicrobial peptide was further added to efficiently kill concomitantly bacteria, yeast and fungi. Moreover, the poly-L-arginine used was not monodisperse, but the commercial batch of poly-L-arginine used was composed of polymeric chains with different chain lengths and a molecular weight of more than 70 000 (which correspond to polypeptide chains having more than 400 arginine residues).

Contrary to this, in context of the present invention, the inventors selected well-defined poly-L-arginine chains having a short chain length from 2 to 10 residues (PAR2 to PAR10) or 30 residues (PAR30), to buildup layer-by-layer coatings with HA as polyanion.

The inventors surprisingly demonstrated that the coatings comprising poly-L-arginine with a chain length of 10 and HA as polyanion showed a strong inhibition of bacterial growth of *S. aureus* for coatings having more than 25 bilayers, for example, 48 layers. These results are unexpected and surprising, in particular, because initial results with coatings comprising PAR10, HA as polyanion and only 24 bilayers did not show biocidal activity under the conditions tested.

The inventors further demonstrated, as a proof of principle, biocidal activity against *M. luteus*, for coatings comprising PAR30, HA as polyanion and 24 bilayers The biocidal activity against *M. luteus* (see FIG. 11) is furthermore surprising and unexpected, because *M. luteus* is hyaluronidase deficient. The inventors thus demonstrated that the biocidal activity of the polyelectrolyte coating of the invention is independent of the degradation of the HA layer, which is contrary to prior art coatings that require the degradation of the HA layer.

Furthermore, contrary to other coatings, the mechanism responsible for the biocidal activity of the coating of the present invention seems to be based on the surface contact of the bacteria with the coating.

The inventors further demonstrated that the short length polycation molecules, such as PAR10 and PAR30, diffuse within the coating and the biocidal activity seems to depend on free diffusion of the polycation molecules, because cross-linking of the coating reduces its biocidal function (see FIGS. 9 and 10).

SUMMARY OF THE INVENTION

The present invention therefore relates to a polyelectrolyte coating, comprising:
(a) at least one polycationic layer consisting of at least one polyarginine consisting of n repetitive arginine units, wherein n is an integer comprised between 2 and 10, and
(b) at least one polyanionic layer consisting of hyaluronic acid.

The present invention also relates to a device comprising the polyelectrolyte coating of the invention.

The present invention further relates to the use of the polyelectrolyte coating of the invention for producing a device of the invention, in particular a medical device, more particularly an implantable device.

The invention further concerns a method for preparing a device comprising the polyelectrolyte coating of the invention, the method comprising:
(a) providing a device;
(b1) depositing on the surface of said device
(i) at least one polycationic layer consisting of at least one polyarginine consisting of n repetitive arginine units, wherein n is an integer comprised between 2 and 10, and then
ii) at least one polyanionic layer consisting of hyaluronic acid, or
(b2) depositing on the surface of said device ii) and then i) as defined above, and optionally repeating step b1) and/or b2).

In a further aspect, the invention refers to a kit comprising
a) at least one polycationic material consisting of at least one polyarginine consisting of n repetitive arginine units, wherein n is an integer comprised between 2 and 10, and
b) at least one polyanionic material consisting of hyaluronic acid.

In a further aspect, the invention refers to a method of preventing a bacterial infection in an individual undergoing an implantation of an implantable device comprising the steps of providing an implantable device as defined herein below, and implanting said implantable device in the individual wherein said implantable device prevents a bacterial infection.

DETAILED DESCRIPTION OF THE INVENTION

Polyelectrolyte Coating

Figure 1:
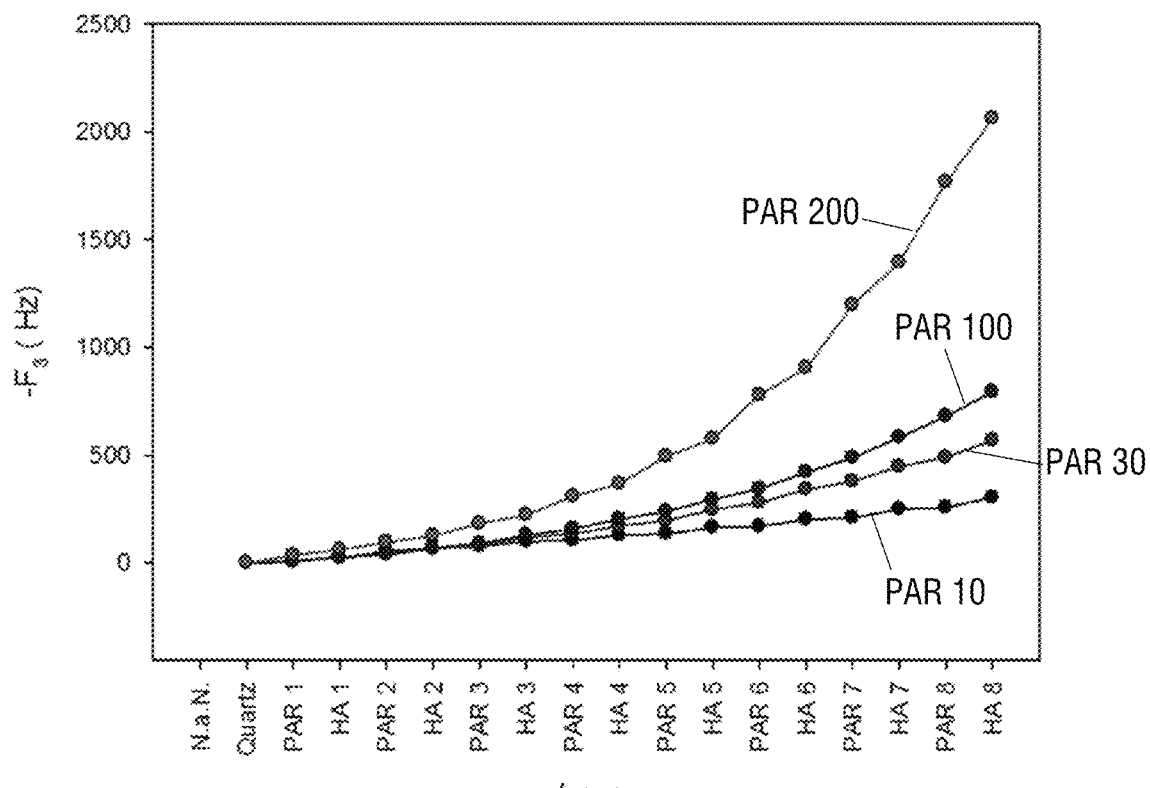
FIG. 1: Graph demonstrating the buildup of (PAR/HA) multilayer coating on a $SiO_2$ coated crystal followed by QCM. Various molecular weight of PAR (10, 30, 100 or 200 residues corresponding to notation PAR10 PAR30, PAR100 or PAR200 respectively) are used in association with HA. Evolution of the normalized frequency $-\Delta fv/v$ (for v=3) as a function of the number of layers adsorbed. An exponential growth of the normalized frequency with the number of deposition step was observed for coatings buildup with PAR30, PAR100 or PAR200. The most important growth was monitored for larger PAR chains. In the case of PAR10 the increment in the normalized frequency with the deposition number is the weaker, however an exponential growth was already observed.

The inventors of the present inventions have demonstrated that a polyelectrolyte coating with polyarginine as polycation and hyaluronic acid (HA) as polyanion is a powerful surface coating with biocidal properties. The inventors demonstrated that, a polyelectrolyte coating with poly-L-arginine (PAR, in particular, 10 or 30 arginine residues) and hyaluronic acid (HA) as polyanion has strong biocidal activities.

The inventors further demonstrated that, a polyelectrolyte coating with poly-arginine with 10 arginine residues and hyaluronic acid (HA) as polyanion has strong biocidal activity when the polyelectrolyte coatings consist of more than 24 layers, such as 48 layers.

The wording "polyelectrolyte", as known by the skilled in the art, refers to polymers whose repeating units bear an electrolyte group. Polycations and polyanions are both polyelectrolytes. Accordingly, the polyanionic and polycationic layers in context of the invention may be referred to as polyelectrolyte layers.

The word "at least" in "at least one polyarginine" herein refers to at least 1, 2, 3, 4, 5, 6, 7, 8 or 9 polyarginines consisting of n repetitive arginine units, preferably 1, 2, 3, 4, 5, 6, 7, 8, 9, polyarginines, more preferably one, two or three polyarginines consisting of n repetitive arginine units, for example one polyarginine consisting of n repetitive arginine units.

It will be therefore understood that in embodiments, wherein the "at least one" in "at least one polyarginine" refers to more than one polyarginine the "at least one polycationic layer" in context of the invention consists of a mixture of specific polyarginines, wherein the specific polyarginines differ from each other in their chain length. It will be understood by the skilled in the art, that, for example, the at least one polyarginine may refer to, for example, two polyarginines, wherein one polyarginine has a chain length of, for example, 5 (n=5) and the other polyarginine has a chain length of, for instance, 10 (n=10).

As mentioned herein above, polyarginine is a polycation, it will be therefore understood by the skilled in the art, that a "at least one polyarginine consisting of n repetitive arginine units" may as well be referred to as "at least one polycation consisting of n repetitive arginine units" and is a positively charged polymer and can also be referred to as "polycationic material".

Accordingly, in one embodiment, the polycationic material of n repetitive arginine units constitutes the at least one polycationic layer of the polyelectrolyte coating of the invention.

As defined in context of the invention, the "n" of the "n repetitive arginine units" is an integer comprised between 2 and 10.

In a further embodiment, n is an integer comprised between 3 and 10, for example, 4 and 10, 5 and 10, 6 and 10, 7 and 10, 8 and 10, such as 9 or 10, preferably between 4 and 10, more preferably 5 and 10.

In a further embodiment, n is an integer comprised between 2 and 10, for example, 2 and 9, 2 and 8, 3 and 9, 3 and 8, 3 and 7, 4 and 7.

In a further embodiment, n is an integer that is 10 or smaller than 10, is 9 or smaller than 9, is 8 or smaller than 8, is 7 or smaller than 7, is 6 or smaller than 6.

In one embodiment, n is an integer selected from the group consisting of 2, 3, 4, 5, 6, 7, 8, 9, 10, preferably, n is 5 or 10.

The "repetitive arginine unit" can also be called "structural unit" and herein refers to the amino acid arginine, also referred to as arginine residue.

In one embodiment, the n repetitive arginine units polymerize via the formation of a peptide bond. Accordingly, n repetitive arginine units may be referred to as polymer or polypeptide. According to the number of n, the polypeptide may be referred to as di-, tri, tetra-, penta-, hexa-, hepta-, octa, ennea- and deca-peptide for n=2, 3, 4, 5, 6, 7, 8, 9, 10, respectively.

A "peptide bond", also called amide bond, is a covalent chemical bond formed between the carboxyl group (COOH) of one amino acid and the amino group ($NH_2$) of another amino acid, wherein one molecule of water is produced.

"Arginine" is an α-amino acid that is used in the biosynthesis of proteins. Polyarginine refers to a polymer of the structural unit arginine. Polyarginine refers to poly-L-, poly-D- or poly-LD-arginine. In context of the present invention, polyarginine refers, in particular, to poly-L-arginine (PAR).

"Poly-L-arginine" is a positively charged synthetic polymer (also called polycation) and is produced in the form of a salt with a counterion. The counter ion may be selected from, but is not limited to, hydrochloride, hydrobromide or trifluoracetate.

In one example, polyarginine is poly-L-arginine hydrochloride with CAS #26982-20-7.

In one example, poly-L-arginine (PAR) such as PAR10 (10 arginine (R), Mw=2.1 kDa, PDI=1) and PAR5 were purchased from Alamanda Polymers, USA.

Methods to obtain polypeptides having n repetitive units such as polyarginine with for example n=10 arginine units are known to the skilled in the art and include ring-opening polymerization of alpha-amino acid N-carboxyanhydrides (NCAs) followed by purification. Typically, the polypeptides are purified after polymerization by precipitation in water or, for example, in an organic nonsolvent and, after amino acid side chain deprotection, by dialysis. All water-soluble polymers are finally lyophilized.

Methods to obtain copolymers having n arginine units are also known to the skilled in the art.

In one preferred embodiment, the at least one polyarginine refers to one polyarginine consisting of n repetitive units and is monodisperse, i.e. the polycationic material of which the polycationic layer consists is monodisperse. It will be understood by the skilled in the art that if the polycationic material of which the polycationic layer consists is monodisperse, the polycationic layer is as well monodisperse. Accordingly, in one embodiment, the polycationic layer in context of the present invention is monodisperse.

"Monodisperse" herein refers to a polymer consisting of the same molecules having the same mass. Synthetic monodisperse polymer chains can be made, for example, by processes such as anionic polymerization, a method using an anionic catalyst to produce chains that are similar in length, for example, ring-opening polymerization of alpha-amino acid N-carboxyanhydrides (NCAs). It can be concluded on the basis of the polydispersity index (PDI) if a sample of a polymer is monodisperse. Accordingly, in one embodiment, monodispersity is expressed using the polydispersity index (PDI).

In some embodiments, when the at least one polyarginine is more than one polyarginine, then the at least one polyarginine may be polydisperse, i.e. the polycationic material of which the polycationic layer consists is a mixture of different polycations and may be polydisperse. It will be understood by the skilled in the art that if the polycationic material of which the polycationic layer consists is polydisperse, the polycationic layer is as well polydisperse. Accordingly, in one embodiment, the polycationic layer in context of the present invention is polydisperse.

"Polydisperse" herein refers to a polymer consisting of different molecules having a different mass.

The "polydispersity index (PDI)" or "heterogeneity index", or simply "dispersity", is a measure of the distribution of molecular mass in a given polymer sample. The polydispersity index (PDI) is calculated by dividing the weight average molecular weight ($M_w$) with the number average molecular weight ($M_n$). The PDI has a value equal to or greater than 1, but as the polymer chains approach uniform chain length, the PDI approaches 1.

Accordingly, in one embodiment, the polydispersity index (PDI) is smaller than 1.5, smaller than 1.4, smaller than 1.3, in particular between 1 and 1.2, preferably between 1 and 1.1, for example between 1 and 1.05.

In one particular embodiment, the polydispersity index (PDI) of the polyarginine, the polycationic material or the polycationic layer is smaller than 1.5, smaller than 1.4, smaller than 1.3, in particular between 1 and 1.2, preferably between 1 and 1.1, for example between 1 and 1.05.

As known by the skilled in the art the PDI may be measured by size-exclusion chromatography (SEC), light scattering measurements such as dynamic light scattering measurements or mass spectrometry such as matrix-assisted laser desorption/ionization (MALDI) or electrospray ionization mass spectrometry (ESI-MS).

In one example, the PDI is measured either on the protected polyamino acids by, typically, gel permeation chromatography (GPC) in, for example, DMF with 0.1M LiBr at typically 60° C. or on the deprotected polypeptides by, for example, GPC in typically aqueous buffer using, in both cases, a calibration curve that was constructed from narrow polydispersity PEG standards or universal calibration of TALLS. The average molecular weight is provided by TALLS or by proton NMR spectroscopy using the amino acid repeating unit to incorporated initiator peaks integration ratio.

"Hyaluronic acid (HA)" also known as Hyaluronan is a linear (unbranched) polysaccharide or non-sulfated glycosaminoglycan, composed of repeating disaccharide units of N-acetyl glucosamine and glucuronate (linked by β 1-3 and β 1-4 glycosidic bonds). Hyaluronic acid (HA) thus is a negatively charged polymer (also called polyanion) and is therefore, in context of the present invention, also referred to as polyanionic material. Said negatively charged polymer therefore exists together with a counter ion in form of a salt. For sodium hyaluronate the counterion is sodium. It is distributed widely throughout connective, epithelial and neural tissues as part of the extra-cellular matrix. There are high concentrations in the vitreous and aqueous humor of the eye, synovial fluid, skin, and the umbilical cord (Wharton jelly). The average 70-kg man has roughly 15 grams of hyaluronan in his body, one-third of which is turned over (degraded and synthesized) every day. It is an evolutionarily conserved molecule being found in both the group A and C Streptococci and *Pasteurella multocida* as well as birds, mammals, and other orders of animals. In solutions of moderate to high molecular weight (500,000 to >3 million Da) at low concentrations it imparts considerable viscosity to aqueous solutions. Hyaluronic acid can be degraded from Hyaluronidase. The molecular weight (Mw) of hyaluronan represents an average of all the molecules in the population and thus represents the molecular Mass Average (Molecular Weight Average). In one example, Hyaluronic acid has a molecular weight of 150 kDa and is brought in form of Sodium Hyaluronate from Lifecore Biomed, USA.

"Hyaluronidase" is a family of enzymes that degrade hyaluronan. The enzyme is found in most animal species and many micro-organisms. There are a number of different types of hyaluronidase with different specificity and kinetics.

In one embodiment, the polyelectrolyte coating of the invention may further comprise a "pharmaceutical active drug".

In the context of the present specification the term "pharmaceutical active drug" refers to compounds or entities which alter, inhibit, activate or otherwise affect biological events. For example, the drug includes, but is not limited to, anti-cancer substances, anti-inflammatory agents, immunosuppressants, modulators of cell-extracellular matrix interaction including cell growth inhibitors, anticoagulants, antithrombotic agents, enzyme inhibitors, analgetic, antiproliferative agents, antimycotic substances, cytostatic substances, growth factors, hormones, steroids, non-steroidal substances, and anti-histamines. Examples of indication groups are, without being limited thereto analgetic, antiproliferativ, antithrombotic, anti-inflammatory, antimycotic, antibiotic, cytostatic, immunosuppressive substances as well as growth factors, hormones, glucocorticoids, steroids, non-steroidal substances, genetically or metabolically active substances for silencing and transfection, antibodies, peptides, receptors, ligands, and any pharmaceutical acceptable derivative thereof. Specific examples for above groups are paclitaxel, estradiol, sirolimus, erythromycin, clarithromycin, doxorubicin, irinotecan, gentamycin, dicloxacillin, quinine, morphin, heparin, naproxen, prednisone, dexamethason.

In one embodiment, the "pharmaceutical active drug" is the polycationic material as defined herein above.

In one embodiment, the polyelectrolyte coating of the invention is biocompatible.

The term "biocompatible" as used in context of the invention, intends to describe a coating that does not elicit a substantial detrimental response in vivo.

As mentioned herein above, the inventors of the present invention demonstrated surprisingly that the polyelectrolyte coatings of the invention have biocidal activity.

Accordingly, in one embodiment, the polyelectrolyte coating of the invention has biocidal activity.

"Biocidal activity" herein refers to destroy, deter, render harmless, or exert a controlling effect on any harmful organism. A biocidal activity herein refers, for example, to an antimicrobial activity.

"Antimicrobial activity" herein refers to antiseptical, antibiotic, antibacterial, antivirals, antifungals, antiprotozoals and/or antiparasite activity, preferably antibacterial activity.

Accordingly, in one embodiment, the polyelectrolyte coating of the invention has antibacterial activity and/or bacteriostatic activity.

In one embodiment the antibacterial activity and/or bacteriostatic activity is directed against at least one bacterium.

"Bacteriostatic activity" herein refers to stopping bacteria from reproducing, while not necessarily killing them, in other words bacteriostatic activity herein refers to inhibiting the growth of bacteria. Accordingly, bacteriostatic activity may be expressed, for example, in % of growth inhibition of at least one bacterium.

The "growth inhibition of at least one bacterium" in context of the present invention, may be more than 70%, for example, more than 75%, more than 80%, typically, more than 82, 84, 86, 88, 90, 91, 92, 93, 94, 95, 96, 97, 98%. Accordingly, in one embodiment, the polyelectrolyte coating of the invention has more than 70% growth inhibition of at least one bacterium, more particularly, more than 75%, more than 80%, typically, more than 82, 84, 86, 88, 90, 91, 92, 93, 94, 95, 96, 97, 98% growth inhibition of at least one bacterium.

The "at least one bacterium" herein refers to bacteria of at least 1, 2, 3, 4, 5, 6, 7, 8, 9, 10 or more species of bacteria.

In one particular example, the growth inhibition in context of the present invention, is measured by using *S. aureus* as at least one bacterium and the normalized *S. aureus* growth is measured after 24 h, after 18 h, or after 12 h, preferably 24 h contact with the polyelectrolyte coating of the invention.

In one embodiment, the at least one bacterium is an ESKAPE pathogen.

The "ESKAPE pathogens" are the leading cause of nosocomial infections throughout the world and are described in, for example, Biomed Res Int. 2016; 2016: 2475067. In one embodiment, the term "ESKAPE pathogens" refers to a bacterium selected from the group constituted of *Enterococcus faecium, Staphylococcus aureus, Klebsiella pneumoniae, Acinetobacter baumannii, Pseudomonas aeruginosa*, and *Enterobacter* species.

In one embodiment, the at least one bacterium is a gram-positive bacterium or gram-negative bacterium, preferably gram-positive bacterium.

In one embodiment, the gram-negative bacterium is a *Pseudomonas aeruginosa, Acinetobacter baumannii, Stenotrophomonas maltophilia, Escherichia coli, Klebsiella pneumoniae, Enterobacter* species or *Legionella* bacterium, preferably, *Escherichia coli* or *Pseudomonas aeruginosa*

In one embodiment, the gram positive bacterium is a *Staphylococcus, Micrococcus* or *Enterococcus* bacterium.

Bacteria of the "*Staphylococcus*" genus are stationary, non-spore-forming, catalase-positive, oxidase-negative, gram-positive cocci grouped together in grape-like clusters. Observed by Pasteur in 1879 in furuncle pus, staphylococci owe their name to Ogsten (1881) who isolated them in acute chronic abscesses. Bacteria of the "*Staphylococcus*" genus, such as, for example, *S. aureus, S. epidermidis, S. capitis, S. caprae, S. haemolyticus, S. lugdunensis, S. schleiferi, S. simulans* and *S. warneri* are the main agents of infections on foreign materials for example in prosthetic joint infections.

Accordingly, in one embodiment the *Staphylococcus* is selected from *S. aureus, S. epidermidis, S. capitis, S. caprae, S. haemolyticus, S. lugdunensis, S. schleiferi, S. simulans* and *S. warneri*, preferably *S. aureus* and *S. epidermidis*, more preferably *S. aureus*.

Bacteria of the "*Micrococcus*" genus are generally thought to be a saprotrophic or commensal organism, though it can be an opportunistic pathogen, particularly in hosts with compromised immune systems, such as HIV patients. Micrococci are normally present in skin microflora, and the genus is seldom linked to disease. However, in rare cases, death of immunocompromised patients has occurred from pulmonary infections caused by *Micrococcus*. Micrococci may be involved in other infections, including recurrent bacteremia, septic shock, septic arthritis, endocarditis, meningitis, and cavitating pneumonia in particular in immunosuppressed patients.

In one embodiment the *Micrococcus* is a *M. luteus* bacterium.

Bacteria of the "*Enterococcus*" genus are the cause of important clinical infections such as urinary tract infections, bacteremia, bacterial endocarditis, diverticulitis, and meningitis.

In one embodiment the *Enterococcus* is a vancomycin-resistant *Enterococcus*, such as *E. faecalis* or *E. faecium*.

The bacteriostatic activity or % of growth inhibition may be demonstrated, for example, in an antibacterial assay as herein described in the section "methods" herein below. Strains that may be used in such an antibacterial assay may be, for example, *M. luteus* or *S. aureus*.

As mentioned in the introduction herein above, in one typical application, the polyelectrolyte coating of the present invention particularly aims at preventing nosocomial infections related to implants and medical devices. In said context, the risk of an infection is especially high during the 6 hours post-implantation.

Accordingly, in one embodiment, the polyelectrolyte coating of the present invention has a biocidal activity, in particular an antibacterial activity and/or bacteriostatic activity, within the first 24 hrs post implantation, for example within the first 12 hrs, first 9 hrs, first 6 hrs post implantation.

As further mentioned in the introduction, antibacterial coatings have a vast field of applications. Accordingly, in one embodiment the polyelectrolyte coating of the invention has an anti-fouling activity.

"Fouling" or "Biofouling" or "biological fouling" herein refers to the accumulation of microorganisms on a wetted surface.

"Anti-fouling" therefore herein refers to inhibiting the accumulation of microorganisms on a wetted surface.

The polyelectrolyte coating of the present invention is typically constructed using a layer-by-layer (LbL) deposition technique as further described in the section "Method for preparing a device" herein below. Based on the layer-by-layer structure the polyelectrolyte coating might also be referred to as a "polyelectrolyte multilayer (PEMs)", "polyelectrolyte film" or "polyelectrolyte matrix".

Each of the polyelectrolyte layers has its given charge. The polycationic layer and the polyanionic layer, both form a polyelectrolyte network or a polyelectrolyte backbone. The polyelectrolyte layers attract each other by electrostatic interactions. Other attractive forces are based on hydrophobic, van der Waals, and hydrogen bonding interactions.

In general, during LbL deposition, a device, such as, for example, a medical device or an implantable device is dipped back and forth between dilute baths of positively and negatively charged polyelectrolyte solutions. During each dip a small amount of polyelectrolyte is adsorbed and the surface charge is reversed, allowing the gradual and controlled build-up of electrostatically cross-linked polycation-polyanion layers. It is possible to control the thickness of such coatings down to the single-nanometer scale.

Accordingly, the polyelectrolyte coating of the invention typically includes substantially ordered polyelectrolyte layers of alternatingly charged polyelectrolyte layers.

In one embodiment, a single polyelectrolyte layer, such as one polycationic or polyanionic layer, has a thickness of 1 nm to 10 nm. The thickness of the polycationic and/or polyanionic layer depends on the coating conditions and the polyelectrolyte material used.

In one embodiment, the polyelectrolyte coating has a thickness which is typically substantially thicker than the thickness of a single polyelectrolyte layer of the polyelectrolyte coating. In one embodiment, the polyelectrolyte coating may have a thickness of about 10 nm to about 100 000 nm. The thickness of the polyelectrolyte coating depends on the coating conditions, the number of, and the polyelectrolyte material used for, the polyelectrolyte layers.

The thicknesses of an obtained polyelectrolyte coating may be evaluated, for example, using confocal microscopy. Therefore, for example, 100 µL of PLL-FITC (poly-L-lysine labeled with fluorescein isothyocyanate, a green fluorescent probe) (typically 0.5 mg·mL$^{-1}$ in Tris-NaCl buffer) are deposited on top of a polyelectrolyte coating, for example a (PAR30/HA)$_{24}$ polyelectrolyte coating. After 5 minutes and diffusion of PLL-FITC through the whole polyelectrolyte coating, a rinsing step is typically performed with Tris-NaCl buffer. Observations of the coatings may be carried out with a confocal microscope, such as Zeiss LSM 710 microscope (Heidelberg, Germany) using a 20× objective (Zeiss, Plan Apochromat).

As described above, the polyelectrolyte coating may be formed in a self-assembled manner to produce a Layer-by-Layer (LbL) structure.

The term "layer" in "polycationic layer" or "polyanionic layer" herein refers to an amount of polycations or polyanions as defined herein above, for example, deposited on, for example, the surface of a device, wherein said device is as defined herein below in the section "device" and may be, preferably, a medical device or an implantable device. As it will be understood by the skilled in the art, in context of the invention, one polycationic layer may consist of several layers of the same polycationic material, and one polyanionic layer may consist of several layers of the same polyanionic material. However, as it will be further understood by the skilled in the art, even if one polycationic or polyanionic layer may consist of several layers, those layers will be referred to as one layer in context of the present invention. Accordingly, the term polycationic layer as used in context of the present invention refers to the entire polycationic material that is located between two polyanionic layers and the term polyanionic layer as used in context of the present invention refers to the entire polyanionic material that is located between two polycationic layers.

In some embodiments, "at least one polycationic layer" and/or "at least one polyanionic layer" in context of the invention refers to at least 25, at least 26, at least 28, at least 30, at least 35, at least 40, at least 45, at least 50, at least 55, at least 60, at least 65, at least 70, at least 75, at least 80, at least 85, at least 90, at least 95, at least 100, at least 200, at least 300, at least 400, at least 500 polycationic layers and/or polyanionic layers.

In some embodiments "at least one polycationic layer" and/or "at least one polyanionic layer" in context of the invention refers to at least 25, at least 26, at least 28, at least 30, at least 35, at least 40, at least 45, at least 50, at least 55, at least 60 polycationic layers and/or polyanionic layers, preferably at least 30, at least 40, at least 45 polycationic layers and/or polyanionic layers.

In some embodiments, "at least one polycationic layer" and/or "at least one polyanionic layer" refers to 30 to 500 polycationic and/or polyanionic layers, for example 30 to 400, 30 to 300, 30 to 200, 30 to 100, 30 to 90, 30 to 80, 35 to 80, 40 to 80, such as 40 to 75, 40 to 70, 40 to 60 preferably 25, 30, 32, 34, 36, 38, 40, 42, 44, 46, 48, 50, 52, 54, 56, 58, 60 layers.

In certain embodiments the number of the polycationic layers and the number of the polyanionic layers are the same.

In certain embodiments, the polycationic and polyanionic layers are alternating layers, in particular alternating charged polyelectrolyte layers.

Accordingly, in one embodiment, the polyelectrolyte coating comprises 30 to 150 polycationic layers and/or 30 to 150 polyanionic layers, preferably the polyelectrolyte coating comprises 30 to 100 polycationic layers and/or 30 to 100 polyanionic layers, more preferably, the polyelectrolyte coating comprises 30 to 80 polycationic layers and/or 30 to 80 polyanionic layers.

In one example, as further described herein below, it is possible to cover the surface of an object with one polycationic layer, to wash the object and cover it again with one polycationic layer. These steps can be repeated several times in order to obtain one polycationic layer of a specific thickness which thus consists of several polycationic layers. As it will be understood by the skilled in the art this procedure can be used as well to obtain one polyanionic layer of a certain thickness which is thus constituted of several polyanionic layers.

In one example, the polyelectrolyte coating consists of 30 layers of polyarginine having 10 arginine residues (PAR10) and 30 layers of HA, accordingly said coating will herein be called (PAR10/HA)$_{30}$. In the same example, the first layer is a polycation layer consisting of PAR10, followed by a first layer of the polyanion HA, followed by a second polycation layer consisting of PAR10 and followed by a second polyanion layer consisting of HA. The layers are alternating until the $30^{th}$ polycation layer consisting of PAR10 and the $30^{th}$ polyanion layer consisting of HA.

In another example, the polyelectrolyte coating consists of 48 layers of polyarginine having 10 arginine residues (PAR10) and 48 layers of HA, accordingly said coating will herein be called (PAR10/HA)$_{48}$. In the same example, the first layer is a polycation layer consisting of PAR10, followed by a first layer of the polyanion HA, followed by a second polycation layer consisting of PAR10 and followed by a second polyanion layer consisting of HA. The layers are alternating until the $48^{th}$ polycation layer consisting of PAR10 and the $48^{th}$ polyanion layer consisting of HA.

In a further aspect of the invention, the polyelectrolyte coating may also, for example, start with a polyanionic layer on the surface of an object and finish with a polyanionic layer, in that case the number of the polycationic and polyanionic layers are different. Preferably, the polyelectrolyte coating starts with a polyanionic layer, for instance, when the surface of the object is positively charged.

In another aspect of the invention, the polyelectrolyte coating may also, for example, start with a polycationic layer on the surface of an object and finish with a polycationic layer; in that case the number of the polycationic and polyanionic layers is as well different. Accordingly, in certain embodiments the number of the polycationic layers and the number of the polyanionic layers are different. Preferably, the polyelectrolyte coating starts with a polycationic layer when the surface of the object is negatively charged.

In one example, the polyelectrolyte coating consists of 49 layers of polyarginine having 10 arginine residues and 48 layers of HA, accordingly said coating will be called (PAR10/HA)$_{48}$/PAR10.

Accordingly, in certain embodiments the number of the polycationic layers and the number of the polyanionic layers differ by one layer.

In certain embodiments, different polyelectrolyte layers consist of the same polycationic material or of different polycationic materials as herein defined. For example, the polyelectrolyte coating may comprise 24 layers consisting of polyarginine having 10 arginine residues and 24 layers consisting of polyarginine having 5 arginine residues and 48 layers consisting of HA.

The inventors of the present invention observed an exponential growth of the normalized frequency with the number of deposition steps for the build-up of the polyelectrolyte coatings with PAR10, PAR30, PAR100 or PAR200 and HA using quartz crystal microbalance (QCM), as further explained in the examples and FIG. 1. The inventors further demonstrated that the exponential increase of the thickness with the number of depositing step is related to the diffusion, in and out of the whole coating, of at least one polyelectrolyte constituting the multilayer. The inventors further demonstrated using bleaching experiments that the polycationic polymer contained in the coating is mobile and thus diffuses inside the whole coating, as demonstrated in FIGS. 7 and 8.

Accordingly, in one embodiment, the polyelectrolyte coating of the invention raises with an "exponential growth", as called in the literature, of the normalized frequency with the number of deposition steps.

In a further embodiment, the "polyarginine consisting of n repetitive arginine units", i.e. the individual peptide chains are mobile and/or diffuse within the polyelectrolyte coating.

It has been shown by the inventors in context of PAR30, that the covalent coupling of the at least two oppositely charged polyelectrolyte layers reduces the bacteriostatic activity of the coating. Since PAR30 and PAR10 are similar in their mobility in the coating, it will be understood by the skilled in the art that this observation can be transferred to polyarginine having a shorter chain length. Accordingly, in one embodiment the at least one polycationic layer and the at least one polyanionic layer are not covalently coupled.

Device

Staphylococcal infections on foreign material differ from conventional infections by the arrangement of bacteria in the form of biofilm.

"Biofilm" is a complex three-dimensional structure which is connected to the foreign material and in which the bacteria cells are embedded in a polysaccharide extracellular matrix called slime or glycocalyx. This specific structure may be formed by bacteria of the same species or of different species. In comparison with their living congeners in free (or 'planctonic') form, these bacteria are in a state of quiescence indicated by a low level of metabolic activity. Due to the reduced metabolic activity bacteria in the form of a biofilm are, for example, more resistant to any antibacterial treatment.

The problematic of biofilms is not limited to the medical field. Biofilms are ubiquitous, occurring in aquatic and industrial water systems as well as a large number of environments. Biofilms can avidly colonize the surfaces of a wide variety of household items such as toilet bowls, sinks, toys, cutting boards, and countertops in kitchen and bathrooms. Biofilms may also occur in the food production industry, either in tins or on the machines that are used along the production lines. At water and sewage treatment facilities, biofilms (biofouling) are also problematic: they cause metal corrosion, increased risk of contamination of products, decreased quality of water, and reduced efficacy of heat exchange for example for boards, and countertops in kitchen and bathroom.

Accordingly, an antibacterial coating is an advantage for devices in many different applications.

As described above, the inventors of the present invention developed a polyelectrolyte coating having a biocidal activity. The inventors demonstrated for coatings comprising PAR10, in particular for (PAR10/HA)$_{48}$, that the polyelectrolyte coating has a biocidal activity, in particular within the first 24 hours when contacted with a solution containing bacteria, more preferably the first 12, first 6 hours when contacted with a solution containing bacteria, such as *S. aureus*.

The inventors further demonstrated for coatings comprising PAR30, in particular for (PAR30/HA)$_{24}$, that the polyelectrolyte has a biocidal activity, in particular within the first 72 hours when contacted with a solution containing bacteria, in particular within the first 48 hours when contacted with a solution containing bacteria, more preferably the first 24, first 12, first 6 hours when contacted with a solution containing bacteria.

The polyelectrolyte coating of the present invention therefore inhibits growth of a bacterium and thus prevents bacteria from the formation of a biofilm of the surface of a device comprising the polyelectrolyte coating of the invention.

The inventors demonstrated, for example, that (PAR/HA)$_{24}$ coatings built with PAR30 after 24/48 or 72 h of incubation show a total inhibition of bacteria which demonstrate their efficiency over 3 days and three successive contaminations.

The inventors further discovered that the time period of the biocidal activity of the coatings of the invention increases with the number of layers.

Accordingly, the time period of the biocidal activity of the coating of the present invention increases with the number of layers used.

The inventors further demonstrated that neither drying nor sterilization of the coatings of the invention did modify the antimicrobial activity of the coating.

Accordingly no change in the total bactericide activity was measured even after sterilization.

It will be therefore be understood by the skilled in the art that due to the bactericide activity of the polyelectrolyte coating of the invention, said polyelectrolyte coating is particularly suitable for producing a device comprising said polyelectrolyte coating.

Accordingly, the present invention further refers to a device comprising a polyelectrolyte coating of the invention.

A "device" herein refers to an object comprising at least one surface.

In one embodiment, the polyelectrolyte coating covers at least a portion of the surface of said device.

In one embodiment, the surface of the device of the present invention comprises, consists of, or at least partly consists of metal such as titanium, plastic such as silicone, ceramic or other materials such as wood.

In a further embodiment, the surface of the device of the present invention exists in any kind of architecture depending on the material used, accordingly, it will be understood by the skilled in the art, that the surface may be a flat surface, or uneven surface, such an uneven surface exists, for example, on surfaces of porous materials such as typically foams or fibers. In some examples, the surface may also comprise or consist of micro or nanoparticles.

Since the device comprises the polyelectrolyte coating of the invention, it will be understood by the skilled in the art, that, therefore, the features associated with said polyelectrolyte coating that are further defined above in the section "polyelectrolyte coating" also refer to said device.

Accordingly, in one embodiment, the device of the invention has biocidal activity, wherein the biocidal activity is as defined in the section "polyelectrolyte coating" herein above.

In one aspect of the invention, the device of the invention has more than 70% growth inhibition of at least one bacterium, more particularly, more than 75%, more than 80%, typically, more than 82, 84, 86, 88, 90, 91, 92, 93, 94, 95, 96, 97, 98% growth inhibition of at least one bacterium. % growth inhibition of at least one bacterium is as defined herein above in the section "polyelectrolyte coating".

In one embodiment, the growth inhibition is preferably measured with *S. aureus* wherein a solution inoculated with *S. aureus* is contacted with the polyelectrolyte coating for 24 hours.

In a further embodiment, the device of the present invention has a biocidal activity or bacteriostatic activity within the first 72 hours post implantation, for example within the first 48 hours, 24 hours, 12 hours, first 9 hours, and first 6 hours post implantation.

In a preferred embodiment, the device of the present invention has a biocidal activity or bacteriostatic activity within the first 24 hours post implantation, for example within the first 12 hours, first 9 hours, and first 6 hours post implantation.

Furthermore, in one embodiment the device of the invention has anti-fouling activity. In a further embodiment, the device of the invention has antibacterial activity and/or bacteriostatic activity.

Accordingly, in one embodiment, the device comprising a polyelectrolyte coating of the invention is a bacteriostatic device and/or a fouling resistant device. Bacteriostatic is as defined herein above in the section "polyelectrolyte coating".

The polyelectrolyte coating of the invention and the device of the invention can be easily sterilized and stored without detrimental effects to the coating and its properties.

It will be further understood by the skilled in the art that due to the biocidal and/or bacteriostatic activity of the polyelectrolyte coating of the inventions, said polyelectrolyte coating is, in one embodiment particularly suitable for producing a medical device, preferably an implantable device.

A "medical device" herein refers to an instrument, apparatus, implement, machine, contrivance, implant, in vitro reagent, or other similar or related article, including a component part, or accessory which is for example intended for use in the diagnosis of disease or other conditions, or in the cure, mitigation, treatment, or prevention of disease, in an individual as defined herein below, or intended to affect the structure or any function of the body of an individual, and which does not achieve any of its primary intended purposes through chemical action within or on the body of man or other animals and which is not dependent upon being metabolized for the achievement of any of its primary intended purposes. In one example, a medical device refers to a device used for wound healing, such as bandages, for example adhesive bandages or dressings. In a further example, a medical device refers to sanitary articles.

A medical device herein may be destinated for use in an individual.

The term "individual", "patient" or "subject" refers to a human or non-human mammal, preferably a mouse, cat, dog, monkey, horse, cattle (i.e. cow, sheep, goat, buffalo), including male, female, adults and children.

Accordingly, in one embodiment, the medical device in context of the invention may be a medical instrument.

In one embodiment, a medical instrument may be selected from the group consisting of a percussion hammer, pleximeter, thermometer, foreign body detector, stethoscope, specula, forceps, otoscope, or any accessories thereof, probes, retractors, scalpel, surgical scissors, bone instruments, sharps spoons, suture needles and wounds clips.

In one embodiment, the medical device is an implantable device.

The "implantable device" of the present invention refers to a piece of equipment or a mechanism that is placed inside of the body of an individual to serve a special purpose or perform a special function.

An implantable device, in context of the present invention, may be, for example, a prosthetic device or, for example, a device implanted to deliver medication, nutrition or oxygen, monitor body functions, or provide support to organs and tissues. Implantable devices may be placed permanently or they may be removed once they are no longer needed. For example, stents or hip implants are intended to be permanent. But chemotherapy ports or screws to repair broken bones can be removed when they no longer needed.

In one embodiment, the implantable device is selected from the group comprising catheters, arteriovenous shunts, breast implants, cardiac and other monitors, cochlear implants, defibrillators, dental implants, maxillofacial implants, middle ear implants, neurostimulators, orthopedic devices, pacemaker and leads, penile implants, prosthetic devices, replacement joints, spinal implants, voice prosthesis, artificial hearts, contact lenses, fracture fixation device, infusion pumps, intracranial pressure device, intraocular lenses, intra-uterine devices, joint prosthesis, prosthetic valves, orthopedic devices, suture materials, urinary stents, vascular assist device, vascular grafts, vascular shunts and vascular stents, and artificial vessels of permanent or transient types.

In a preferred embodiment, the implantable device is selected from the group comprising catheters, defibrillators, prosthetic devices, prosthetic valves, replacement joints, orthopedic devices, pacemakers, vascular grafts, vascular shunts, vascular stents and intra-uterine devices, preferably catheters, orthopedic devices, pacemakers and prosthetic devices.

A "catheter" herein refers to a tubular medical device for insertion into canals, vessels, passageways, or body cavities for diagnostic or therapeutic purposes, fluids and medication, but also in drainage of body fluids such as urine or abdominal fluids; angioplasty, angiography, and catheter ablation; administration of gases such as oxygen and volatile anesthetic agents and hemodialysis.

A "shunt" typically refers to a narrow metal or plastic tube that diverts blood from one part to another.

A "stent" typically refers to a short narrow metal or plastic tube often in the form of a mesh that is inserted into the lumen of an anatomical vessel as an artery or bile duct especially to keep a previously blocked passageway open.

A "prosthetic valve" is for example a prosthetic heart valve.

Method for Preparing a Device of the Invention

The present invention further refers to a method for preparing a device of the invention herein referred to as the method of the invention.

The device of the invention may comprise different materials as specified herein above, accordingly the at least one surface of the device to be covered with the polyelectrolyte coating may comprise different materials as specified herein above. It will be understood by the skilled in the art that said materials differ in their surface charge. Positively charged surfaces are, for example, the surfaces consisting of amine group based polymers. Negatively charged surfaces are for example the surfaces consisting of carboxylic groups based polymers. It will be further understood by the skilled in the art, that a positively charged surface will be first covered with a polyanionic layer and then with a polycationic layer, wherein a negatively charged surface will be first covered with a polycationic layer and then with a polyanionic layer. The two consecutive deposition steps may then be repeated as often as needed.

In one example, a device of the invention is prepared by depositing on, for example, its $SiO_2$ surface 48 bilayers of PAR/HA $(PAR10/HA)_{48}$ using, for example, an automated dipping robot, such as the an automated dipping robot of Riegler & Kirstein GmbH, Berlin, Germany. Therefore, the surface of the device is typically first washed with, for example, Hellmanex® II solution at 2%, $H_2O$, and ethanol and dried with air flow. Solutions of polyelectrolytes such as PAR and HA are prepared, for example, by dissolving PAR and HA at typically 0.5 mg·mL$^{-1}$ in buffer containing typically 150 mM NaCl and, for example, 10 mM of tris(hydroxymethyl)-aminomethane (TRIS, Merck, Germany) at, typically, pH 7.4. The surface of the device is dipped alternatively in polycation and polyanion solutions and extensively rinsed in NaCl-Tris buffer between each step. After preparation, the coating is, typically, dried with air flow and then immerged in NaCl-Tris buffer and stored at 4° C. before use.

The wording "depositing on the surface of said device at least one polycationic layer" and "depositing on the surface of said device at least one polyanionic layer" of step b1) i) and ii) or b2) ii) and i) herein refers to contacting the surface of said device with a polycationic solution in case of step b1) i) or b2 i) or to contacting the surface of said device with a polyanionic solution in case of step b1) ii) or b2 ii).

The "surface of said device" herein refers to at least one surface, said at least one surface may be partially covered by the polyelectrolyte coating of the invention. The at least one surface is preferably one surface.

A "polycationic solution" or "polyanionic solution" herein refers to a solution comprising polycationic material or polyanionic material as defined herein above in the section "polyeletrolyte coating". In context of the present invention, typically a "polycationic solution" and a "polyanionic solution" might be referred to as polyelectrolyte solution.

In one example, the polycationic solution herein refers to a solution comprising at least one polyarginine consisting of n repetitive arginine units, wherein n is an integer between 2 and 10.

In one example, the polyanionic solution herein refers to a solution comprising hyaluronic acid.

"Contacting" as herein used refers typically to spraying, immersing, dipping or pouring.

Accordingly, in one embodiment, for "depositing the polyelectrolyte layers according to step (b1) and/or (b2)", a polyelectrolyte solution may, for instance, be sprayed onto the surface of a device on which the polyelectrolyte coating is to be formed.

Alternatively, or in combination, the surface of said device can be immersed or dipped into a polyelectrolyte solution or a polyelectrolyte solution can be poured onto the surface of the substrate.

Accordingly, in one embodiment, the at least one polycationic layer is deposited on the surface of the device in step b1) i) by contacting the surface of said device with a polycationic solution comprising at least one polyarginine consisting of n repetitive arginine units as defined herein above.

Accordingly, in one embodiment, the at least one polyanionic layer is deposited on the surface of the device in step b1) ii) by contacting the surface of said device with a polyanionic solution comprising HA.

It will be understood that the steps b1) and/or b2) may be repeated as often as necessary by the skilled in the art in order to obtain a device comprising a polyelectrolyte coating with the number of polyelectrolyte layers, in particular alternating polycationic and polyanionic layers, as defined herein above in the section "polyelectrolyte coating". It will be clear to the skilled in the art, that the deposition of the polyelectrolytes may be influenced by the pH.

Accordingly, in one embodiment, said "polycationic solution" and/or "polyanionic solution" in context of the invention may further comprise a buffer.

A "buffer" is an aqueous solution consisting of a mixture of a weak acid and its conjugate base or a weak base and its conjugate acid. Its pH changes very little when a small amount of strong acid or base is added to it and thus it is used to prevent changes in the pH of a solution. Buffer solutions are used as a means of keeping pH at a nearly constant value in a wide variety of chemical applications. Buffers used in the context of the invention might be, for example, PBS (Phosphate buffered saline) or TRIS (tris(hydroxymethyl) aminomethane).

In one embodiment, said "polycationic solution" and/or "polyanionic solution" in context of the invention has pH ranging from 4 to 9, preferably 4, 4.5, 5, 5.5, 6, 6.5, 7, 7.5, 8, 8.5, 9 and typically, a pH ranging from 5 to 8, 5.5 to 8, 6 to 8, 6.5 to 8, 7 to 8, preferably 7 to 8, in particular 7, 7.2, 7.4, 7.6, 7.8, 8, for example 7.4.

It will be further clear to the skilled in the art, that the deposition of the polyelectrolytes may be influenced by the interaction between the charged polyelectrolytes and the charged surface onto which the polyelectrolytes are to be deposited, and the interaction between the charged polyelectrolytes among each other. These interactions can be at least partially controlled by the ion strength of the solution.

Therefore, in some embodiments the ion strength of the polyelectrolyte solution, used in step (b1) or (b2) of the method of the invention is adjusted in certain embodiments to increase the amount of the deposited polyelectrolytes.

Accordingly, in one embodiment, said "polycationic solution" and/or "polyanionic solution" in context of the invention may further comprise ions.

An "ion" is an atom or molecule in which the total number of electrons is not equal to the total number of protons, giving the atom or molecule a net positive (cation) or negative (anion) electrical charge. An ion consisting of a single atom is an atomic or monatomic ion; if it consists of two or more atoms, it is a molecular or polyatomic ion. Ions are further distinct according to the charge they carry. Therefore an ion can be a monovalent ion or bivalent (sometimes called divalent ion) or polyvalent ions. Ions may be without limitation $F^-$, $Cl^-$, $I^-$, $NH_4^+$, $SO_4^{2+}$, $Ca^{2+}$, $Mg^{2+}$, $Na^+$.

Typically, ions may be added in the form of a buffer, as defined herein above, or in the form of a salt, such as for example NaCl.

For example, solutions of polyelectrolytes such as PAR and HA were typically prepared, for example, by dissolving PAR and HA at typically 0.5 mg·mL-1 in sterilized buffer containing typically 150 mM NaCl and, for example, 10 mM of tris(hydroxymethyl)-aminomethan (TRIS, Merck, Germany) at, typically, pH 7.4.

Between the depositions of the polyelectrolyte layers at least one washing or also called rinsing step can be performed in a solution without polyelectrolytes to remove not-assembled polyelectrolyte material.

Accordingly, in one embodiment, the method of the invention further comprises at least one washing step after step i) and/or ii) of b1) or b2).

In one embodiment, for washing, a solution without polyelectrolytes may be used. Said solution may be water or any other solution that seems suitable to the skilled in the art. In one embodiment, washing is performed using buffer, for example NaCl-Tris buffer. In one example, said NaCl-Tris buffer comprises 150 mM NaCl and 10 mM Tris at a pH 7.4.

Alternatively, or in addition to that, in one embodiment, a drying step or steps can be performed.

Accordingly, in one embodiment, the method of the invention further comprises at least one drying step after step i) and/or ii) of b1) or b2) and/or the washing step of claim.

"Drying" may be performed by any method known to the skilled in the art, such as air heating, natural air drying, dielectric drying, air flow, preferably air flow. In one example air flow refers to purging with nitrogen gas.

In one embodiment, after a drying step, the same polyelectrolyte solution as used immediately before the drying step can be deposited again on the surface since the drying can lead to a partial exposure of binding sides or charges of the underlying polyelectrolyte layer, said drying step may therefore also be called an intermediate drying step. By applying such a sequence, the load of a particular polyelectrolyte, can be further increased.

Accordingly, in one embodiment when the method of the invention further comprises at least one drying step the previous step i) or ii) of b1) or b2) and/or the washing step may be repeated.

Typically, a polyelectrolyte solution is brought into contact with the surface and the surface is allowed to dry for a given time, for examples 10 to 60 sec by purging, for example, with nitrogen gas. Subsequently, the same polyelectrolyte solution is again brought into contact with the surface.

In certain embodiments, at least one washing and/or drying step is carried out between two consecutive deposition steps.

It has been shown by the inventors, that the covalent coupling of the at least two oppositely charged polyelectrolyte layers reduces the bacteriostatic activity of the coating.

Accordingly, in one embodiment the method of the invention does not contain a step to covalently couple the at least one polycationic layer with the at least one polyanionic layer.

In one embodiment, the method of the invention further comprises a step (c) wherein the polyelectrolyte coating obtained in steps (a) and (b1) or (b2) of the method as defined above may be further soaked with a pharmaceutical active drug. The pharmaceutical drug is as defined in the section "Polyelectrolyte coating" herein above.

In one particular embodiment, the method for preparing a device is a method for preparing an implantable device.

Accordingly, in one embodiment, the invention refers to a method for preparing an implantable device comprising a polyelectrolyte coating, the method comprising:
(a) providing an implantable device;
(b1) depositing on the surface of said implantable device
(i) at least one polycationic layer consisting of at least one polyarginine consisting of n repetitive arginine units, wherein n is an integer comprised between 2 and 10, and then
ii) at least one polyanionic layer consisting of hyaluronic acid, or (b2) depositing on the surface of said implantable device ii) and then i) as defined above, and optionally repeating step b1) and/or b2).

As described herein above under the section "device", the surface of the device of the present invention comprises, consists of, or at least partly consists of metal such as titanium, plastic such as silicone, ceramic or other materials such as wood. These surfaces may be charged, such as positively or negatively charged. As a result, the skilled in the art will therefore understand that a device comprising a surface that is, for example, negatively charged might be covered first with a cationic layer.

In some embodiments, the device might undergo a surface treatment prior to the method for preparing an implantable device in order to have a charged surface.

Accordingly, the surface of the device provided in step a) might be charged, such as positively charged or negatively charged, wherein the surface is as defined herein above in the section "device".

Alternatively, in some embodiments the method for preparing an implantable device might comprise a step (a2) of charging the surface of said implantable device.

The skilled in the art knows methods to charge the surfaces of a device, such methods include the adsorption of ions, protonation/deprotonation, UV radiations and the application of an external electric field. The skilled in the art further knows, for example, that surface charge practically always appears on a device surface when it is placed into a fluid. Most fluids contain ions, positive (cations) and negative (anions). These ions interact with the device surface. This interaction might lead to the adsorption of some of them onto the surface. If the number of adsorbed cations exceeds the number of adsorbed anions, the surface would have a net positive electric charge, and if the number of adsorbed anions exceeds the number of adsorbed cations, the surface would have a net negative electric charge.

Use

In one embodiment the invention refers to the use of the polyelectrolyte coating of the invention for producing a device of the invention, in particular a fouling resistant device and/or bacteriostatic device.

In a further embodiment the invention refers to the use of the polyelectrolyte coating of the invention for producing a medical device or an implantable device.

Kit

The invention further provides a kit comprising
a) at least one polycationic material consisting of at least one polyarginine consisting of n repetitive arginine units, wherein n is an integer comprised between 2 and 10, and
b) at least one polyanionic material consisting of hyaluronic acid.

In particular, the invention further provides a kit comprising
a) at least one polycationic material consisting of one polyarginine consisting of n repetitive arginine units, wherein n is an integer comprised between 2 and 10, and
b) at least one polyanionic material consisting of hyaluronic acid.

In one embodiment, the kit further comprises instructions regarding the use of the polycationic and polyanionic material. These instructions may e.g. describe a method for preparing an implantable device as defined herein above.

The wording "at least" in "at least one polycationic material" or in "at least one polyanionic material" herein refers to at least 1, 2, 3, 4, 5, 6, 7, 8 polycationic materials.

The word "at least" in "at least one polyarginine" herein refers to at least 1, 2, 3, 4, 5, 6, 7, 8 or 9 polyarginines consisting of n repetitive arginine units, preferably 1, 2, 3, 4, 5, 6, 7, 8, 9, polyarginines, more preferably one polyarginine consisting of n repetitive arginine units.

Therapeutic Methods and Uses

Infections, such as Staphylococcal infections, on foreign material associated with biofilm formation have a number of features which distinguish them completely from conventional tissue infections. These infections are most often paucibacillary (having few bacteria) and readily polymicrobial. The bacteria have a very slow metabolism which keeps them in a state close to dormancy and the genes which they express are different to those activated in planctonic forms. The state of dormancy of the bacteria and the presence of the biofilm significantly reduce the inflammatory reaction and the attraction of immune cells at the infection site. Lastly, for the same reasons, the bacteria are largely protected from the action of antibiotics. It is therefore important to prevent said biofilm formation, in particular, in the body of an individual, for example after transplantation.

The polyelectrolyte coating or implantable device in context of the present invention have a biocidal activity, in particular within the first 72 hours post-implantation, in particular within the first 48 hours post-implantation, more preferably the first 24, first 12, first 6 hours post implantation. The polyelectrolyte coating or implantable device in context of the present invention therefore inhibit growth of a bacterium and thus prevents them from the formation of a biofilm of the surface of said coating or implantable device and thus prevents a bacterial infection.

Accordingly, in one embodiment, the invention refers to a method of preventing a bacterial infection in an individual undergoing an implantation of an implantable device comprising the steps of providing an implantable device as defined herein above, and implanting said implantable device in the individual, wherein said implantable device prevents a bacterial infection.

In one embodiment, providing an implantable device refers to preparing an implantable device according to the method of the invention.

The individual is as defined herein above in the section "device".

In one embodiment, the bacterial infection is a nosocomial infection.

A "nosocomial infection" also called Hospital-acquired infection (HAI) herein refers an infection that is contracted from the environment or staff of a healthcare facility. The infection is spread to the susceptible patient in the clinical setting by a number of means, in particular by implantable devices. Gram positive bacteria involved in "nosocomial infection" are for example *Staphylococcus aureus*. Gram-negative bacteria involved in "nosocomial infection" are for example *Pseudomonas aeruginosa, Acinetobacter baumannii, Stenotrophomonas maltophilia, Escherichia coli, Legionella*.

Accordingly, in one embodiment the nosocomical infection is an infection caused from at least one bacterium as defined above in the section "Polyelectrolyte coating" herein above.

As further specified in the section "device" bacterial infection in form of a biofilm differ from conventional infections.

Accordingly, in one embodiment, the bacterial infection is a biofilm infection.

A "biofilm infection" herein refers to a bacterial infection with biofilm forming bacteria. Biofilm forming bacteria are, for example, but is not limited to, gram-positive bacteria such as *Staphylococcus*, and gram-negative species such as *Escherichia coli*, or *Pseudomonas aeruginosa*.

Any combination of the above embodiments makes part of the invention.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of"). Furthermore the indefinite article "a" or "an" does not exclude a plurality. The mere fact that certain measures are recited in mutually different dependent claims does not indicate that a combination of these measures cannot be used to advantage.

The invention will now be described in more detail with reference to the following examples. All literature and patent documents cited herein are hereby incorporated by reference. While the invention has been illustrated and described in detail in the foregoing description, the examples are to be considered illustrative or exemplary and not restrictive.

EXAMPLES

1. Example 1

1.1 Material

Polyelectrolyte multilayer coatings have been built up with the following polyelectrolytes. Polycations of poly(l-arginine hydrochloride) (PAR) were purchased from Alamanda Polymers, USA. Different PAR polymers used differ from the numbers of arginine per chain: PAR10 10 arginine (R), Mw=2.1 kDa, PDI=1); PAR30 (30 R, Mw=6.4 kDa, PDI, =1.01), PAR100 (100 R, Mw=20.6 kDa, PDI=1.05), and PAR200 (200 R, Mw=40.8 kDa, PDI=1.06). Hyaluronic acid (HA, Mw=150 kDa) used as the polyanion was from Lifecore Biomed, USA.

1.2 Methods

Monitoring Build-Up of Multilayer Coatings:

Coating or film build-up was followed using an in situ quartz crystal microbalance (QCM-D, E1, Q-Sense, Sweden). The quartz crystal is excited at its fundamental frequency (about 5 MHz), as well as at the third, fifth, and seventh overtones (denoted by v=3, v=5, v=7 corresponding respectively to 15, 25, and 35 MHz). Changes in the resonance frequencies ($\Delta f$) are measured at these four frequencies. An increase of $\Delta f/v$ is usually associated to an increase of the mass coupled with the quartz. PAR (i.e. PAR10, PAR30, PAR100 or PAR200) and HA were dissolved at 0.5 mg·mL$^{-1}$ in sterilized buffer containing 150 mM NaCl and 10 mM of tris(hydroxymethyl)-aminomethan (TRIS, Merck, Germany) at pH 7.4. The polyelectrolyte solutions were successively injected into the QCM cell containing the quartz crystal and PAR was the first deposited polyelectrolyte. They were adsorbed for 8 min and then, a rinsing step of 5 min with NaCl-Tris buffer was performed.

Buildup of (PAR/HA)$_{24}$ with Dipping Robot:

For the construction of 24 bilayers of PAR/HA ((PAR30/HA)$_{24}$) an automated dipping robot was used (Riegler & Kirstein GmbH, Berlin, Germany). Glass slides (12 mm in diameter) were first washed with Hellmanex® II solution at 2%, H$_2$O, and ethanol and dried with air flow. The solutions of polyelectrolytes were prepared as described above for QCM experiments. Glass slides were dipped alternatively in polycation and polyanion solutions and extensively rinsed in NaCl-Tris buffer between each step. After construction, the coatings were dried with air flow and then immersed in NaCl-Tris buffer and stored at 4° C. before use. Thicknesses of obtained coatings were evaluated by deposition of 100 μL of PLL-FITC (poly-L-lysine labelled with fluorescein isothyocyanate, a green fluorescent probe) (0.5 mg·mL$^{-1}$ in Tris-NaCl buffer) on top of the PAR/HA multilayer coatings. After 5 minutes and diffusion of PLL-FITC through the whole coating, a rinsing step was performed with Tris-NaCl buffer. Observations of the coatings were carried out with a confocal microscope Zeiss LSM 710 microscope (Heidelberg, Germany) using a 20× objective (Zeiss, Plan Apochromat).

24 bilayers of PLL/HA (PLL30/HA)$_{24}$ and 24 bilayers of PLO/HA (i.e. (PLO30/HA)$_{24}$, (PLO100/HA)$_{24}$ and (PLO250/HA)$_{24}$) were prepared in analogy, wherein PLO or PLL was dissolved at 0.5 mg·mL$^{-1}$ in sterilized buffer containing 150 mM NaCl and 10 mM of tris(hydroxymethyl)-aminomethan (TRIS, Merck, Germany) at pH 7.4.

Other polyelectrolyte coatings, for example polyelectrolyte coatings comprising 48 bilayers of PAR/HA such as (PAR30/HA)$_{48}$ and (PAR10/HA)$_{48}$ were prepared in analogy.

Antibacterial Assays:

*Staphylococcus aureus* (*S. aureus*, ATCC 25923) strains were used to assess the antibacterial properties of the test samples. Bacterial strain was cultured aerobically at 37° C. in a Mueller Hinton Broth (MHB) medium (Merck, Germany), pH 7.4. One colony was transferred to 10 mL of MHB medium and incubated at 37° C. for 20 h, to provide a final density of 10$^6$ CFU·mL$^{-1}$. To obtain bacteria in the mid logarithmic phase of growth, the absorbance at 620 nm of overnight culture was adjusted of 0.001.

Glass slides coated with (PAR/HA)$_{24}$ with PAR10, PAR30, PAR100, are sterilized by using UV-light during 15 minutes, then washed with NaCl-Tris buffer. After washing, each glass slides were deposited in 24-well plates with 300 μl of *S. aureus*, A$_{620}$=0.001, and incubated during 24 hours at 37° C.

For negative control, uncoated glass slides were directly incubated with *S. aureus* using a similar method.

For positive control, Tetracycline (10 μg·mL$^{-1}$) and Cefotaxime (0.1 μg·mL$^{-1}$) were added in *S. aureus* solution in contact with uncoated glass slides.

To quantify bacteria growth or inhibition after 24 h, the absorbance of the supernatant at 620 nm was measured.

The assay was performed similarly for Glass slides coated with (PLL30/HA)$_{24}$, (PLO30/HA)$_{24}$, (PLO100/HA)$_{24}$ and (PLO250/HA)$_{24}$.

The antibacterial assay for *M. Luteus*, *E. Coli* and *P. aeruginosa* were performed in analogy to the bacterial assay described for *Staphylococcus aureus* described above.

Bacteria Live Dead Assay:

To evaluate the health of bacteria which are on the surface, the BacLight™ RedoxSensor™ CTC Vitality Kit (ThermoFischer Scientific Inc., France) was used. This kit provides effective reagents for evaluating bacterial health and vitality. The kit contains 5-cyano-2,3-ditolyl tetrazolium chloride (CTC), which has been used to evaluate the respiratory activity of *S. aureus*. Indeed, healthy bacteria will absorb and reduce CTC into an insoluble, red fluorescent formazan product. Bacteria which are dead or with a slow respiratory activity will not reduce CTC and consequently will not produce red fluorescent product. Finally this kit gives a semi-quantitative estimate of healthy vs unhealthy bacteria. SYTO® 24 green-fluorescent nucleic acid stain (ThermoFischer Scientific Inc., France) is used for counting all bacteria. A solution of 50 mM CTC and 0.001 mM Syto 24 in pure water is prepared. Each glass slides were washed with phosphate-buffered saline buffer, pH=7.4 (PBS) then 270 µl of PBS and 30 µL of CTC/Syto 24 solution were added. The plate were incubated 30 minutes at 37° C., away from light. Each surfaces were observed with confocal microscopy (Zeiss LSM 710 microscope, Heidelberg, Germany), using a 63× objective, immersed in oil. Excitation/Emission wavelength of stains was 450/630 nm for CTC and 490/515 nm for Syto 24.

Biocompatibility Test:

Human fibroblast (CRL-2522 from ATCC/LGC Standards, France) was cultured at 37° C. in Eagle's Minimum Essential Medium (EMEM, ACC/LGC) with 10% of Fetal Bovin Serum (FBS, Gibco/ThermoFicher Scientific Inc., France) and 1% of penicillin streptomycin (Pen Strep, Life Technologies/ThermoFicher Scientific Inc., France). 50 000 cells were incubated in each well of a 24 well-plates during 24 h. Glass slides coated with $(PAR/HA)_{24}$ were incubated simultaneously in a 6 well-plates with 1 mL of medium. After 24 h, the medium of the wells containing cells was removed and replaced by the supernatant that was in contact with the multilayers for 24 h. Human fibroblasts were incubated during 24 h at 37° C. Then, the supernatant was removed and incubated with 10% of AlamarBlue (ThermoFischer Scientific Inc., France) during 2 h. The cell viability was determined by measuring the fluorescence of produced resofurin (Excitation/Emission wavelength=560/590 nm). Cells were washed twice with PBS and fixed with PFA 4% solution during 10 minutes, and then again washed twice with PBS. A solution of Phalloidin was prepared in PBS buffer with 1% of bovin serum albumin (BSA). The staining solution were placed on the fixed cells for 30 minutes at room temperature and washed two times with PBS buffer. A solution of DAPI was prepared and placed on the cells at the same conditions as previously. Fluorescence images were captured using Nikon Elipse Ti-S with 63×PL APO (1.4 NA) objective equipped with Nikon Digital Camera (DS-Q11MC with NIS-Elements software, Nikon, France), and processed with ImageJ (http://rsb.info.nih.gov/ij/). Excitation/Emission wavelength for Rhodamine Phalloidin was 540/565 nm and for DAPI 350/470 nm.

Time-Lapse Microscopy:

Glass slides coated with $(PAR/HA)_{24}$ were sterilized by using UV-light during 15 minutes, then washed with NaCl-Tris buffer. After washing, each glass slides were mounted in a Ludin Chamber (Life Imaging Services, Switzerland) at 37° C., 5% $CO_2$, with 1 mL µl of S. aureus (used as described previously, with $A_{620}$=0.001), stained with Syto 24 during the culture. The time-lapse sequence was performed during 24 h with a Nikon TIE microscope equipped with a 60×PL Apo oil (1.4 NA) objective and an Andor Zyla sCMOS camera (Andor Technology LtD. United Kingdom), was used with Nikon NIS-Elements Ar software (Nikon, France). Phase contrast and fluorescence images were acquired every 5 min for 24 h. Images were processed with ImageJ.

Circular Dichroism:

Circular dichroism (CD) spectra were recorded using a Jasco J-810 spectropolarimeter (Jasco Corporation, UK) as an average of 3 scans obtained using a 0.1 mm path length quartz cuvette at 22° C. from 180 to 300 nm with data pitch of 0.1 nm and a scan speed of 20 nm/min. All spectra were corrected by subtraction of the buffer spectra. Spectra for each PAR were obtained at a concentration of 2 mg·mL$^{-1}$ in NaCl-Tris Buffer. All CD data were expressed as mean residue ellipticity.

Fluorescent Labelling of PAR:

For labeling PAR chains, PAR (15 mg·mL$^{-1}$ in 100 mM $NaHCO_3$ pH 8.3 buffer) was incubated with fluorescein isothiocyanate (FITC, Sigma Aldrich, France) at 1:2 molar ratio of PAR/FITC at room temperature for 3 h. This solution was dialyzed against 1 L of water at 4° C. with a Slide-A-Lyser Dialysis Cassette (Thermo Fischer Scientific Inc, USA), cut-off=3500 MWCO. PAR-FITC was then produced and stored in aliquots of 2 mL (0.5 mg·mL$^{-1}$ in NaCl-Tris buffer).

Release Experiments:

For the first experiment, a multilayer coating (PAR30/$HA)_{24}$ was built by using PAR-FITC. Release experiments were performed at 37° C. during 24 h in presence of MHB medium or a S. aureus/MHB solution ($A_{620}$=0.001). 300 µL of mineral oil were added on the top of the supernatant to prevent any evaporation during the monitoring. The release of PAR-FITC in solution was performed by measuring the fluorescence of the supernatant over time with a spectrofluorimeter (SAFAS Genius XC spectrofluorimeter, Monaco) with excitation/emission wavelength of 488/517 nm. Three samples were studied for each conditions.

For the second experiment, a multilayer film (PAR30/HA) 24 was incubated at 37° C. with two conditions: A) with 300 µl of S. aureus solution A620=0.001 and B) 300 µl of MHB only. After 24 h, the supernatant in contact with the LbL was taken and incubated with a new S. aureus solution to have a final A620=0.001. After 24 h at 37° C., the absorbance at 620 nm was measured. Three samples were studied for each condition.

Fluorescence Recovery after Photobleaching (FRAP) Experiments:

The diffusion coefficient, D, and the proportion of mobile molecules, p, was measured for $(PAR/HA)_{24}$ multilayers containing PAR-FITC by performing photobleaching experiments (FRAP, Fluorescence Recovery After Photobleaching).

A glass slide coated with the multilayer was introduced in a home-made sample holder and immersed in 200 µl of Tris-NaCl buffer. One circular regions (4.4 µm in radius and referred as "R4" in an image of 35 µm×35 µm or 10.6 µm in radius and referred as "R10" in an image of 85 µm×85 µm) were exposed for 700 msec to the laser light set at its maximum power ($\lambda$=488 nm). Then, the recovery of the fluorescence in the bleached area was observed over time. Observations were carried out with a Zeiss LSM 710 microscope (Heidelberg, Germany) using a 20× objective (Zeiss, Plan Apochromat).

Cross-Linking of $(PAR30/HA)_{24}$:

Crosslinking was performed by immersing the (PAR30/HA)24 films in a solution containing EDC (100 mM) and N-hydroxysuccinimide (10 mM) in NaCl (0.15 M) during 15 h at 4° C. Films were rinsed 2 times with a NaCl (0.15 M) solution. The films were immersed in a solution of ethanolamine (1M) during 40 minutes at 4° C. to neutralize all carboxylates functions that have not react. The films were rinsed with NaCl solution and the NaCl-Tris buffer solution was used for the last rinsing step.

1.3 Results

Figure 4:
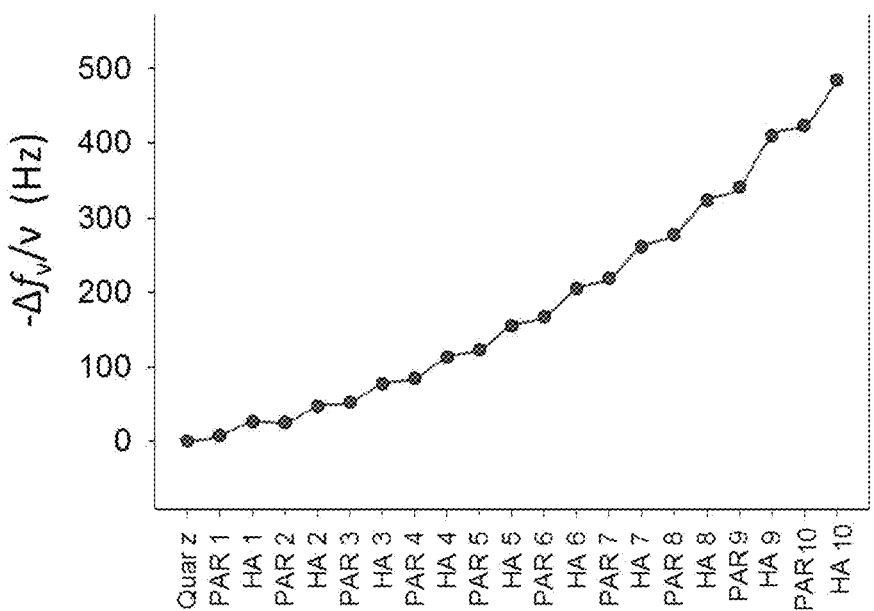
FIG. 4: Graph demonstrating the buildup of $(PAR10/HA)_{10}$ multilayer coating on a $SiO_2$ coated crystal followed by QCM. PAR10 is used in association with HA. Evolution of the normalized frequency $-\Delta fv/v$ (for v=3) as a function of the number of layers adsorbed. The increment in the normalized frequency with the deposition number demonstrates already an exponential growth.

In order to test the buildup of the PAR/HA coatings, quartz crystal microbalance (QCM) was used. FIG. 1 corresponds to the layer-by-layer deposition monitored with QCM for various molecular weight of PAR (10, 30, 100 or 200 residues corresponding to notation PAR10 PAR30, PAR100 or PAR200 respectively). In a first approximation, it is known that the increase in the normalized frequency could be related to an increase in the deposited mass or thickness (REF). An exponential growth of the normalized frequency with the number of deposition step was observed for coatings buildup with PAR30, PAR100 or PAR200. The most important growth was monitored for larger PAR chains (FIG. 1). In the case of $PAR_{10}$ the increment in the normalized frequency with the deposition number is the weaker, however an exponential growth was already observed (FIGS. 1 and 4). Finally, despite the short length of this polypeptide, the layer-by-layer growth was effective.

Figure 5:
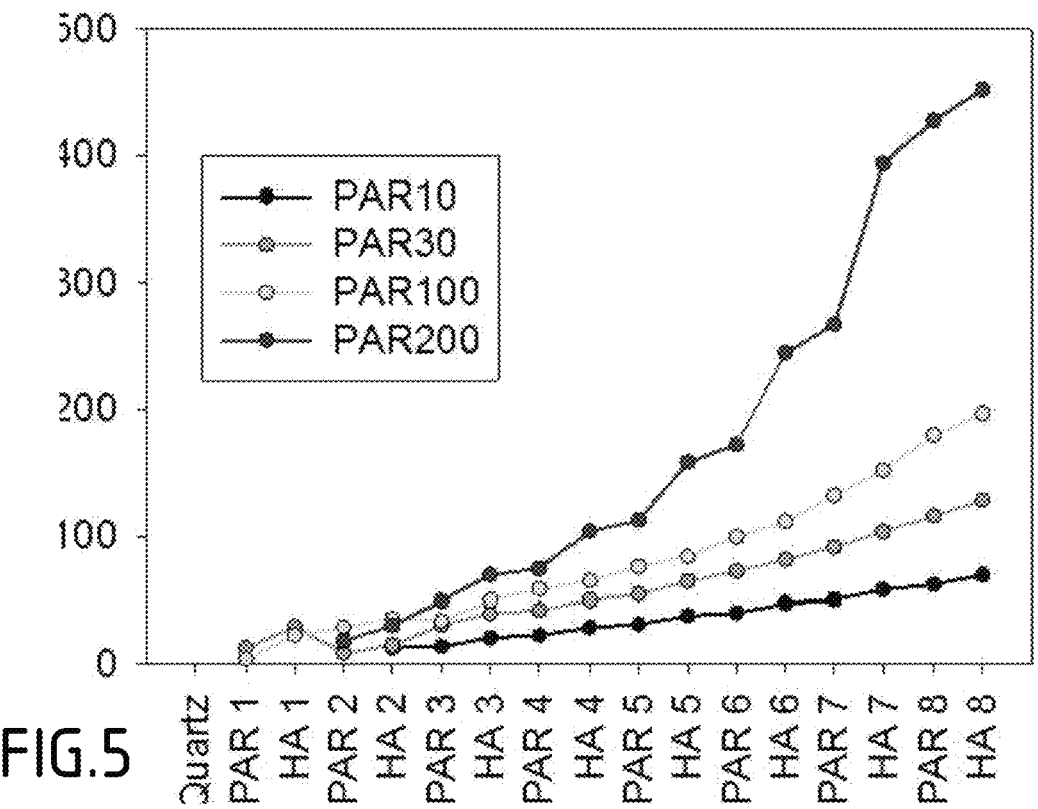
FIG. 5: Graph demonstrating the buildup of (PAR/HA) multilayer coating on a $SiO_2$ coated crystal followed by QCM. Various molecular weight of PAR (10, 30, 100 or 200 residues corresponding to notation PAR10 PAR30, PAR100 or PAR200 respectively) are used in association with HA. Evolution of the estimated thickness as a function of the number of adsorbed layers. An exponential growth of the estimated thickness with the number of deposition step was observed for coatings buildup with PAR10, PAR30, PAR100 or PAR200 (the dark line on the top represent PAR200, then light grey, PAR100, then the third line from the top PAR30, and the black line on the bottom represents PAR10). The most important growth was monitored for larger PAR chains. In the case of PAR10 the increment in the estimated thickness with the deposition number is weaker, however an exponential growth was already observed.
Figure 6:
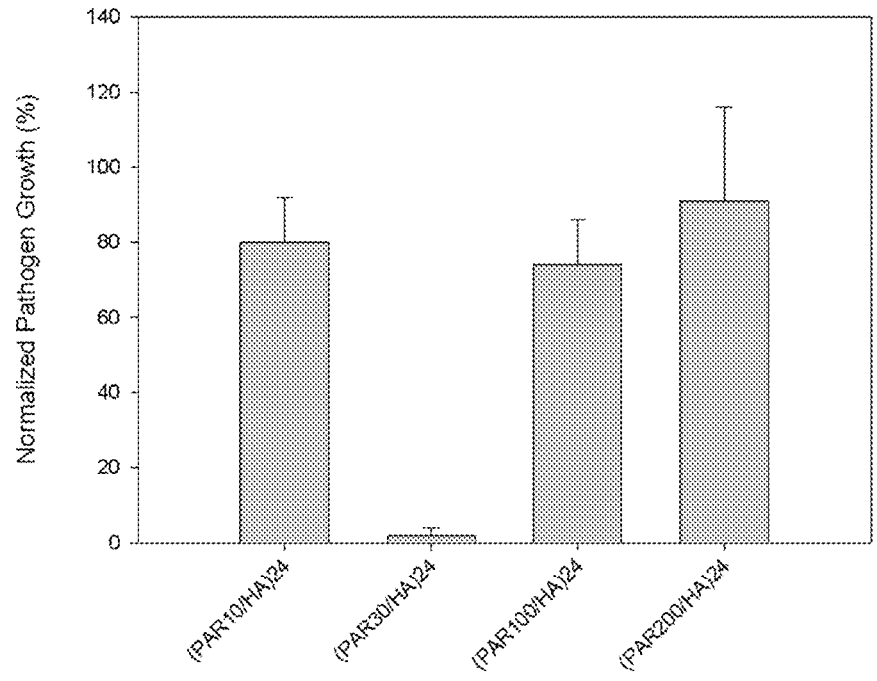
FIG. 6: Graph demonstrating the growth inhibition of S. aureus using different PAR coatings with 24 bi-layers. The normalized S. aureus growth (%) obtained in a supernatant after 24 h in contact with $(PAR/HA)_{24}$ multilayer coatings composed of poly-L-arginine with various number of residues is shown. Each value corresponds to the mean value of 3 experiments and error bars correspond to standard deviations. The growth of S. aureus is about 80% for $(PAR10/HA)_{24}$, 75% for $(PAR100/HA)_{24}$, about 90% for $(PAR200/HA)_{24}$ and less than 5% for $(PAR30/HA)_{24}$ thus showing a strong growth inhibition of more than 95% for $(PAR30/HA)_{24}$.

We also estimated the thicknesses of the films by using the model of Voinova et al. (Phys. Scripta 1999, 59, 391-396). After 8 deposited pair of layers (or "bi-layers") the thicknesses of the films built up with PAR10, PAR30, PAR100 or PAR200 as polycations equals 70, 130, 200 or 450 nm respectively (FIG. 5). Finally for a given number of deposition steps, the thickness increases as the molecular weight of PAR in-creases.

An opposite behavior was previously demonstrated for multilayer coatings buildup with chitosan/HA with various MW of chitosan (Richert 2004, Langmuir). An exponential growth of the coatings was observed for all the MW of chitosan used, however the coating buildup was more rapid when the mass of the chitosan chains was smaller. This behavior was related to the diffusive properties of the chitosan chains in the coatings: shorter chains should diffuse more through the coating which should lead to a higher increase in the mass increment after each layer deposition. However in the present study, experimental conditions are different as an homopolypeptide was selected as the polycation instead of a polysaccharide and the range of their chain length was smaller.

Figure 2:
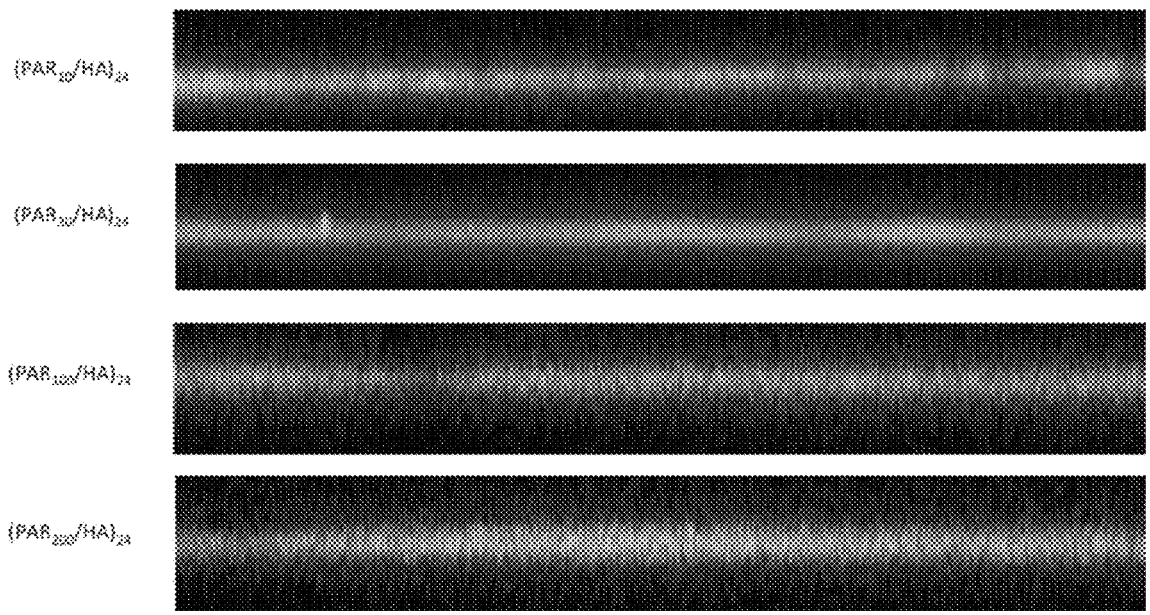
FIG. 2: Image showing the confocal microscopy images of PAR/HA coating sections (x,z). Observation by confocal microscopy of PAR/HA coating sections (x,z) for PAR/HA coating buildups of (PAR/HA) multilayer coating on a $SiO_2$ coated crystal followed by QCM. The Buildup of (PAR/HA) multilayer coating with PAR of various molecular weight was compared, i.e. PAR10 PAR30, PAR100 or PAR200. This image indicates that the obtained coatings were homogenously deposited on the surface in all conditions (for PAR with 10 to 200 residues).

Then, coatings with 24 bilayers ($(PAR/HA)_{24}$) were observed with confocal microscopy. In order to label fluorescently the coatings, poly(lysine)-FITC was added as the last layer on top of the coatings. Cross-section images of coatings build up with PAR of different residue numbers depict thick bands with a green labeling through the whole coating section (FIG. 2). This indicates that the coatings produce were homogenously deposited on the surface in all conditions (for PAR with 10 to 200 residues).

Next, the antimicrobial properties of $(PAR/HA)_{24}$ multilayers for PAR of different number of residues was evaluated. The films were tested against a gram positive bacteria, S. aureus, a strain well known to be associated with nosocomial infections and more particularly with implant-related infections. For example in the case of orthopaedic implants, S. aureus with S. epidermis is involved in 70% of infections (biomaterials 84, 2016, 301). S. aureus were incubated for 24 h at 37° C. in the presence of MHB medium on the $(PAR/HA)_{24}$ coatings. The bacteria were incubated at high density on surfaces for 24 h at 37° C. in the presence of MHB medium. The normalized growth of pathogens (%) was estimated by comparing absorbance at 620 nm in the presence of multilayer films in comparison with the positive control (without multilayer films and in presence of antibiotics in the medium) and the negative control (without multilayer films and in the absence of antibiotics in the medium). No significant inhibition was observed for films built with PAR10, PAR50, PAR100 and PAR200. However, for PAR30 (30 residues), more than 95% of bacterial growth inhibition was observed after 24 hours. This suggests that PAR30 strongly impact viability of S. aureus. It must be pointed out that the molecular weight effect is extremely striking and up to now such an effect on the multilayer film functionality, whatever this function, was never observed (see FIG. 3).

To evaluate more precisely the health of bacteria in contact with the surfaces, the respiratory activity of S. aureus using 5-cyano-2,3-ditolyl tetrazolium chloride (CTC) was monitored. Healthy bacteria will absorb and reduce CTC into an insoluble, red fluorescent formazan product and bacteria which are dead will not reduce CTC and consequently will not produce fluorescent product (Data not shown). A total inhibition of bacteria on (PAR30/HA) surfaces was clearly observed and it was extremely rare to find an area with few bacteria (Data not shown). Comparatively, PAR10, PAR100 or PAR200 surfaces did not prevent bacterial adhesion and growth, a similar density of healthy bacteria as on non-treated surfaces was found. This outstanding result is in full correlation with growth inhibition in supernatant described above where PAR30 was also the only coating strongly effective against bacteria.

Figure 11:
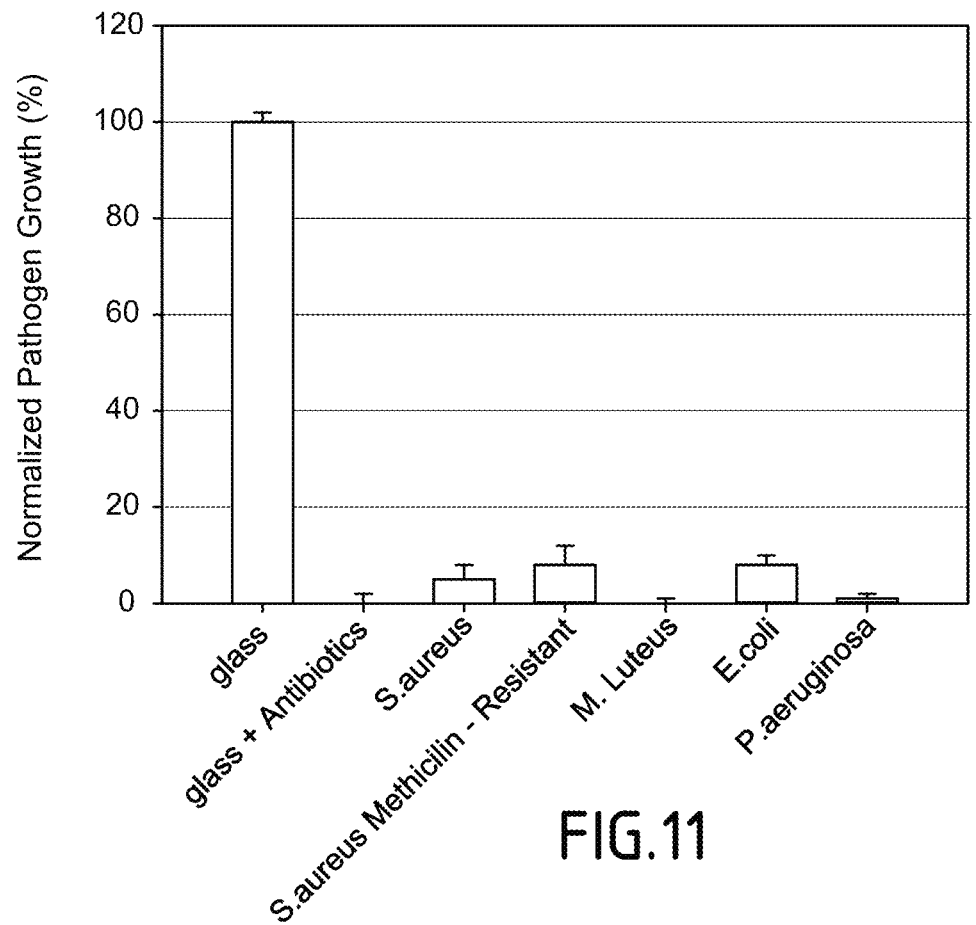
FIG. 11: Graph demonstrating the growth inhibition of different bacteria using $(PAR30/HA)_{24}$ Normalized Growth of bacteria after 24 h in contact with glass covered with the coating $(PAR30/HA)_{24}$. Bacteria growth is inhibited by more than 90% for S. aureus, methilicin resistant S. aureus, M. Luteus, E. Coli and P. aeruginosa.
Figure 12:
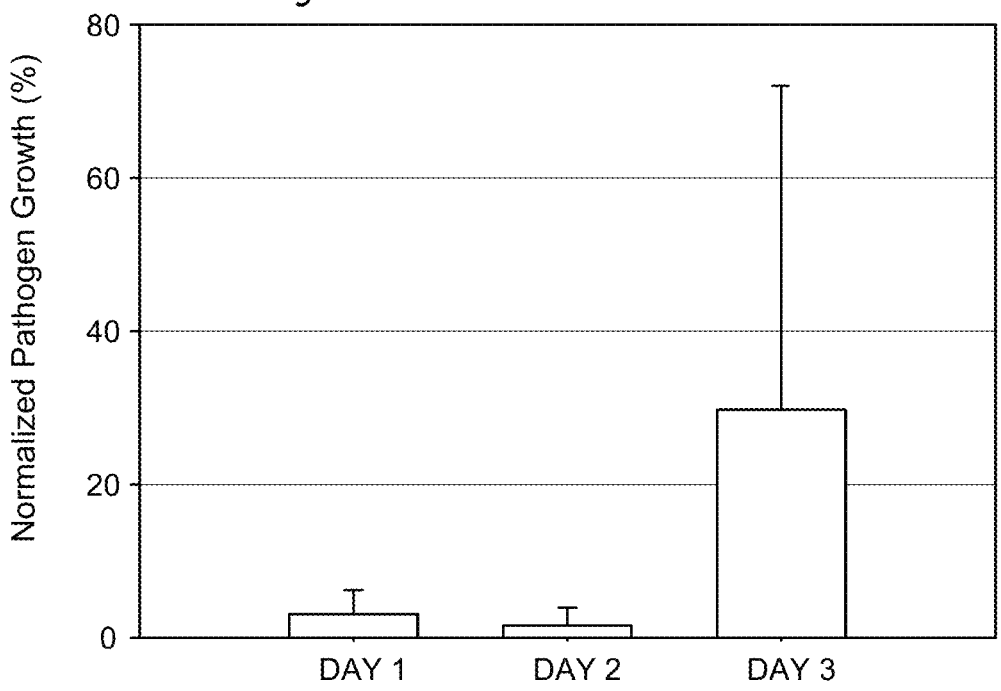
FIG. 12: Graph demonstrating the growth inhibition of S. aureus over time using $(PAR30/HA)_{24}$. The normalized S. aureus growth (%) obtained in a supernatant after 1 day, 2 days and three days in contact with $(PAR30/HA)_{24}$ multilayer coating is shown. The coating was put in contact with a fresh suspension of S. aureus after each 24 h. Each value corresponds to the mean value of 3 experiments and error bars correspond to standard deviations. The growth of S. aureus is less than 5% for $(PAR30/HA)_{24}$ after 1 and 2 days, thus showing a strong growth inhibition of more than 95% for $(PAR30/HA)_{24}$ in the first 48 hrs. After the 3 day the inhibitory activity is reduced.

In order to elucidate if the bacterial growth inhibition of the $(PAR/HA)_{24}$ coatings is only limited to S. aureus, bacterial growth inhibition of $(PAR30/HA)_{24}$ was further tested against other gram positive and gram negative bacteria. Accordingly, the antimicrobial properties of $(PAR30/HA)_{24}$ multilayer was evaluated for methicillin resistant S. aureus strain, M. Luteus, E. coli and P. aeruginosa. The result shown in FIG. 11 demonstrates that the coating has an antibacterial activity against different gram negative and gram positive bacteria.

Figure 3:
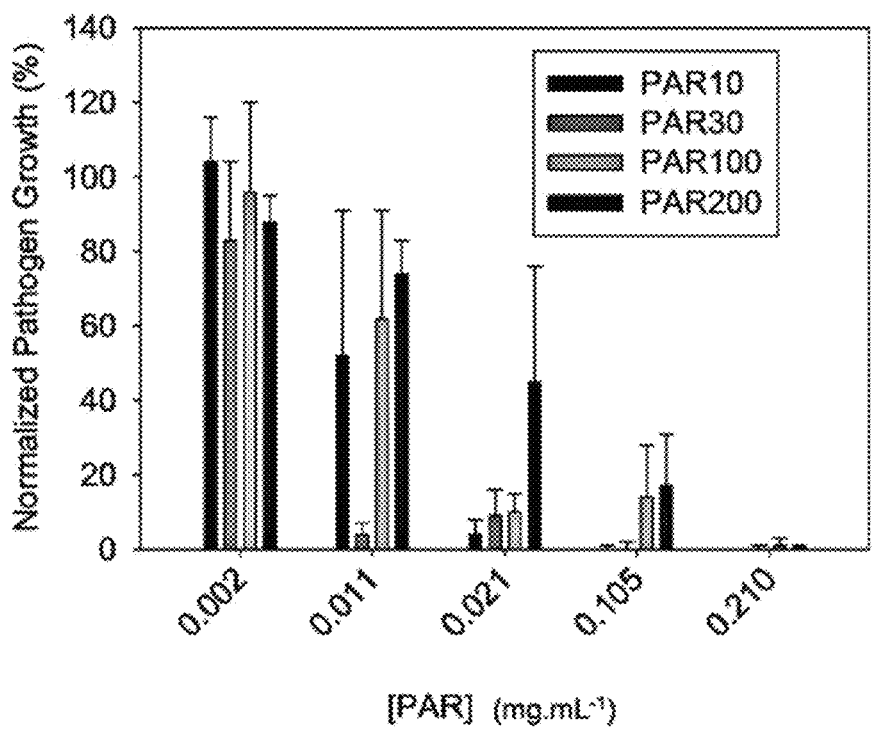
FIG. 3: Graph demonstrating the normalized pathogen growth of S. aureus as a function of PAR concentration ($mg*mL^{-1}$) measured in solution. PAR with 10, 30, 100 or 200 arginine residues per chain were tested. Each PAR was incubated 24 h at 37° C. in 300 μL of MHB medium with S. aureus (A620=0.001). Pathogen growth of 0% corresponds to medium with antibiotics (and without PAR) and 100% to medium without PAR. Each value corresponds to the mean value of 3 individual experiments (3 samples per experiment and condition) and error bars correspond to standard deviations. For each concentration, the first column represents the normalized pathogen growth of S. aureus for PAR10, the $2^{nd}$ column for PAR30, the third column for PAR100 and the fourth for PAR200.

In the following the inventors of the present invention wanted to further elucidate the underlying mechanism that confer to the coatings of the invention the strong inhibitory property on the surface and in the supernatant. As an example the $(PAR30/HA)_{24}$ coating was further investigated. Accordingly, the minimal inhibitory concentration (MIC) of PAR in solution was determined using bacterial assay as described in Experimental Section. For concentrations up to 0.04 $mg \cdot mL^{-1}$, all PAR (PAR10, PAR30, PAR100 or PAR200) totally inhibited S. aureus growth (FIG. 3). However when PAR concentrations were decreased, a difference between the PAR efficiencies was observed: a quasi total inhibition of S. aureus growth was monitored for all PAR at concentrations of 0.02 $mg \cdot mL^{-1}$ except for the longer one, i.e. PAR200 where only a partial inhibition (about 45%) was measured. Finally for PAR at concentrations of 0.01 $mg \cdot mL^{-1}$, inhibition of 100% was shown only for PAR30. Longer or shorter PAR chains (PAR10, PAR100 or PAR200) inhibits only partially (less than 40%) S. aureus growth. This suggests that PAR30 is more effective in solution. This reasoning is valid when PAR concentration values are expressed in mass ($mg \cdot mL^{-1}$) thus it is related to the number of arginine monomers. However when the graph is plotted with concentrations in µM (and thus proportional in number of chains), which means that concentration is related to number of chains, different interpretation can be made (Data not shown). At low concentrations, longer chains are more effective: at 1 µM, PAR100 and PAR200 totally inhibit bacterial growth about 90% growth whereas for a similar effect PAR30 and PAR10 needs to be at about 10 µM. Finally, the inventors of concluded from these results that all PAR chains are effective in solution to inhibit S. aureus growth at concentrations of 0.2 mg·mL. For a given mass of PAR chains in the supernatant, PAR30 is the most effective. Moreover the $MIC_{100}$ values obtained for PAR30, PAR100 or PAR200 ranges at very low concentrations (between 1 and 2 µM) which is remarkable when compared to well-known antimicrobial peptides (for example 30 µM for cateslytin with S. aureus, see Adv. Funct. Mater. 2013, 23, 4801-4809). PAR is thus a powerful candidate to fight against S. aureus.

However, PAR chains of different number of residues were not markedly different in their activity in solution and thus the origin of the PAR30 activity ob-served with PAR30/HA films is not related to its higher activity in solution.

To address the conformations of PAR chains and to check if PAR30 chains have a specific secondary structure that could explain their inhibitory properties compare to longer or shorter chains, circular dichroism (CD) experiments were performed. Firstly, secondary structures of PAR chains in NaCl/TRIS buffer solution (150 mM NaCl, 10 mM Tris, pH 7.4) (Data not shown). All CD spectra of PAR chains (PAR10, PAR30, PAR100 and PAR200) show a unique negative minimum at about 200 nm characteristic of a random coil conformation in solution. In a second step, PAR conformation in PAR/HA multilayer coatings was monitored (Data not shown). Surprisingly, spectra of the coatings depict totally different profiles: no more minima at 200 nm were observed, however one minima at about 10 and another one at about 222 nm were monitored, except for (PAR10/HA)$_{24}$, which present a unique negative minimum at 200 nm (random coil). They can probably not be attributed to HA chains as it is known that in solution at pH 7.4 they have an unordered conformation (Zahouani, ACS Applied Materials, 2016, 8, 14958-14965). Moreover the PAR/HA spectrum corresponds more probably to chains in α-helix conformations characterized by these two minimums. This indicates that PAR chains should change from a coil conformation in solution to an α-helix in the coating. Similar behavior were previously observed for LbL build up with polylysine and poly(glutamic acid) (Boulmedais F. et al. Langmuir, 2002, 18, 4523). Interestingly, unordered antimicrobial peptides are known to adopt an α-helix conformations when they interact with the bacterial membrane and this mechanism is a key point in their mechanism of action (Porcellini F. et al. 2008, Biochemistry, 47, 5565 and Lugardon K. et al., 2001, *J Biol Chem.*, 276(38): 35875). Here in polyelectrolyte multilayer coatings, PAR chains already adopt an α-helix conformation most probably due to the interactions between PAR and HA and local high concentration of PAR. This mechanism can be helpful to fight faster and in a more efficiency way against invading bacteria.

But, because the films built with different PAR chain lengths present similar spectra, the secondary structure of PAR chains cannot explain the striking molecular weight effect on the bactericidal property of the PAR30/HA films.

In view of the absence of specific properties of PAR30 in solution compared to shorter or longer PAR chains, the antimicrobial abilities of PAR30/HA films should be related to the film property by itself. In this context, the inventors investigated if the bactericidal property of the film is due to the release of PAR30 chains from the multilayer into the solution or if bacteria need to come in contact with the film to be killed. For this purpose two types of experiments were performed. Using fluorescently labelled PAR30 chains we first determined the release of PAR30 chains into the solution containing solely MH medium with and without *S. aureus*. Indeed, a slow release process over a time scale of the order of 24 h was observed but it clearly comes out that even after 24 h the PAR30 concentration reached in solution lies significantly below the corresponding MIC concentration: PAR30 released is about 0.18 μM after 24 h while MIC90 is about 2 μM (data not shown). Moreover, when the supernatant, after 24 h of contact with the film, was brought in contact with suspension containing bacteria at a final concentration identical to previous experiments, absolutely no bacteria growth inhibition was observed, confirming that the MIC was not reached in supernatant (data not shown). Finally, we also performed an experiment where bacteria were brought in contact with a (PAR30/HA)$_{24}$ film for 24 hours. Bacteria growth was totally inhibited. The supernatant of this experiment was removed and brought it in contact with a fresh suspension of bacteria. Here again, the bacteria growth was no further inhibited (data not shown). These results demonstrate that the release of the PAR30 chains from the film in the supernatant cannot be at the origin of the bactericidal effect. Finally we can hypothesize that the bactericidal effect is directly related to the contact of the bacteria with the PAR30/HA film which acts as a contact-killing multilayer.

Figure 7:
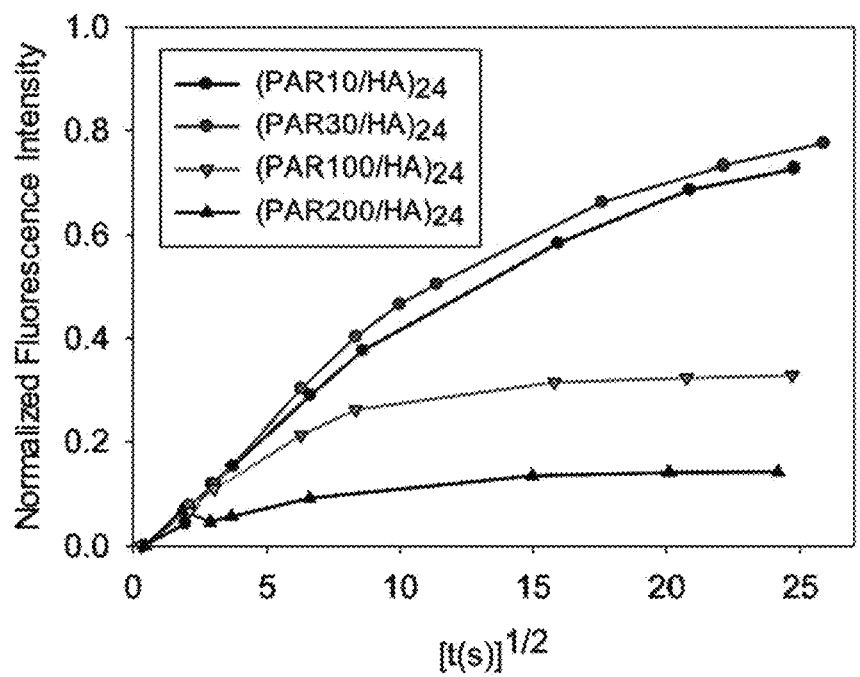
FIG. 7: Graph demonstrating normalized fluorescence intensity of a photobleached area according to $[t(s)]_{1/2}$ for different PAR coatings. Different films $(PAR10-FITC/HA)_{24}$, $(PAR30-FITC/HA)_{24}$, $(PAR100-FITC/HA)_{24}$ and $(PAR20-FITC/HA)_{24}$ are studied by using fluorescence recovery after photobleaching (FRAP) method. t=0 corresponds to the end of the photobleaching step. Accordingly, the evolution of the normalized fluorescence in the bleached area is demonstrated as a function of the square root of time. Recovery of fluorescence appears very fast for PAR10 ($2^{nd}$ line from top of the graph) and PAR30 ($1^{st}$ line from top of the graph) compare to PAR100 ($3^{rd}$ line from top of the graph) or PAR200 ($4^{th}$ line from top of the graph).
Figure 8:
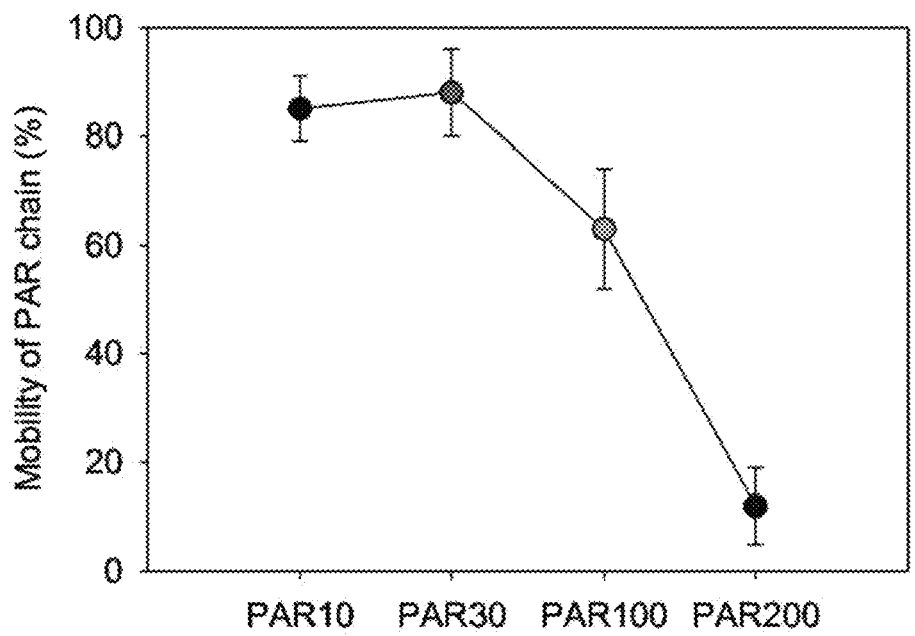
FIG. 8: Graph demonstrating the mobility of the different PAR chains. Proportion of mobile PAR (%) is estimated from data in FIG. 7. PAR10 and PAR30 chains are more mobile (between 85 to 90% of mobile fraction) than the PAR100 (only 63% of mobile fraction). The largest chains PAR200 correspond to the slowest with about 12% of the population which is mobile.

Then the inventors investigated if the bactericidal activity of the PAR30/HA multilayer is related to the mobility of these chains in the films. Indeed, it is known that the exponential character of a multilayer is related to the diffusion ability of at least one of its constituents in and out of the film during each deposition step. They first determined the mobility of the different chains, PAR10, PAR30, PAR100 and PAR200 in the (PAR/HA)$_{24}$ multilayer by using FRAP method. FIG. 7 shows the evolution of the normalized fluorescence in the bleached area as a function of the square root of time. Recovery of fluorescence appears very fast for PAR10 and PAR30 compare to PAR100 or PAR200. From these curves we can deduce the percentage of mobile chains over the timescale of the experiments. It clearly appears that PAR10 and PAR30 chains are more mobile (between 85 to 90% of mobile fraction) than the PAR100 (only 63% of mobile fraction). The largest chains PAR200 correspond to the slowest with about 12% of the population which is mobile (FIG. 8). Accordingly, the fraction of mobile chains dramatically decreases when the chain length increases from 30 to 100 or 200 residues.

Figure 9:
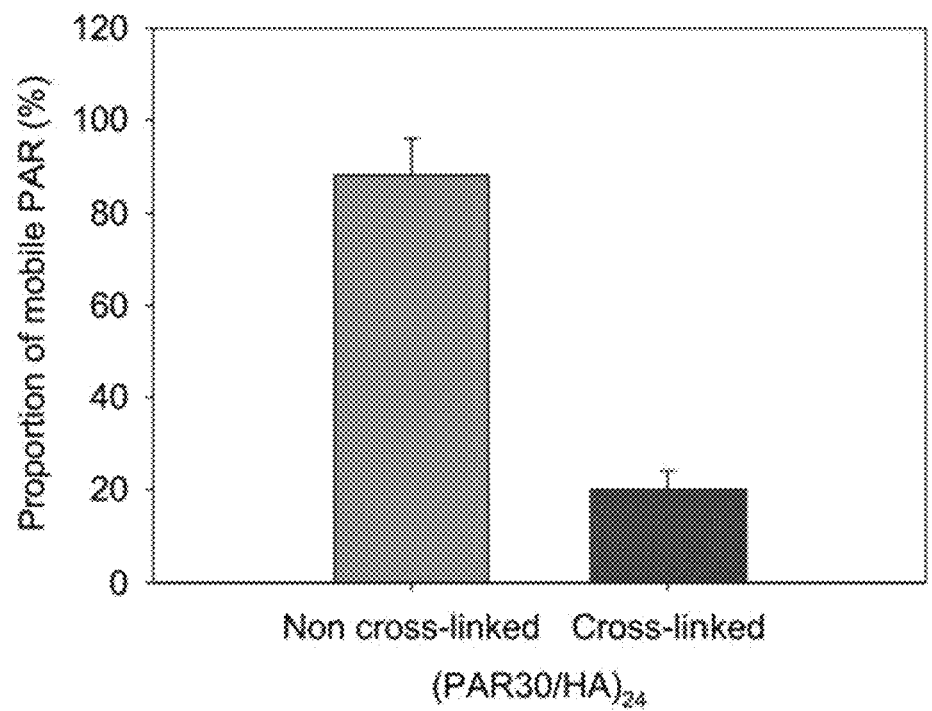
FIG. 9: Graph demonstrating the mobility of PAR in $(PAR30/HA)_{24}$ or crosslinked $(PAR30/HA)_{24}$. $(PAR30/HA)_{24}$ was cross-linked using EDC/NHS with 0.5 M EDC and 0.1M NHS for 15 h at 4° C. Unreacted carboxyl groups were neutralized using ethanolamine. The Proportion of mobile PAR (%) is estimated for $(PAR30\text{-FITC}/HA)_{24}$ compared to $(PAR30\text{-FITC}/HA)_{24}$ that has been cross-linked with EDC-NHS. The proportion of mobile chains measured by FRAP method decreases significantly from 88% for the non-cross-linked film to 20% for the cross-linked one
Figure 10:
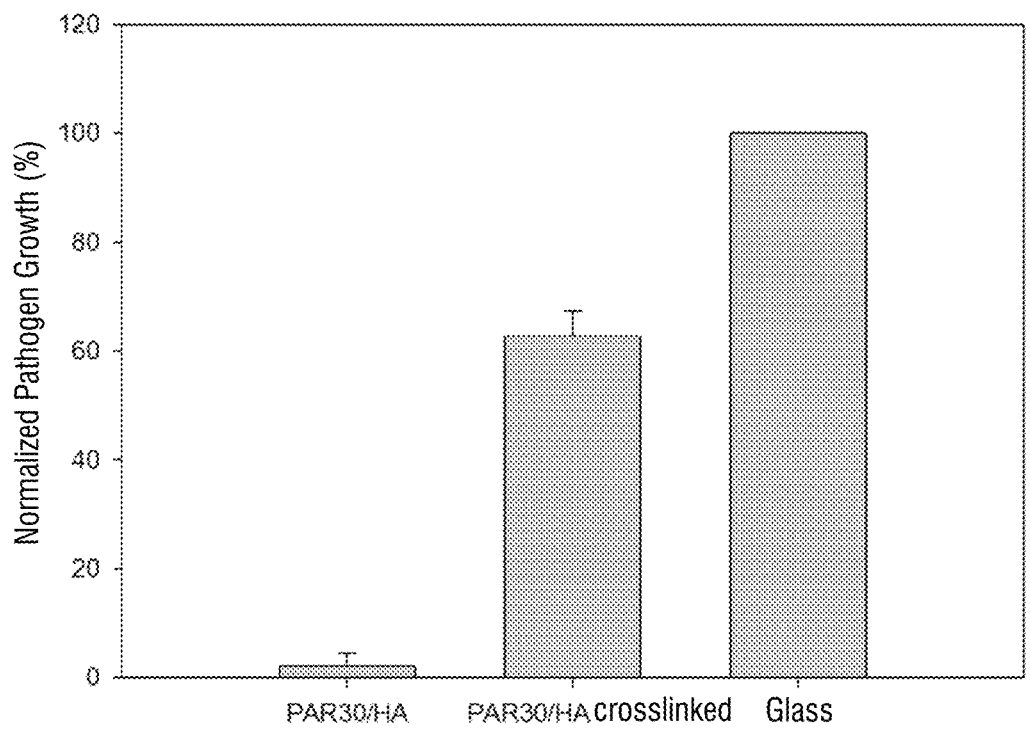
FIG. 10: Graph demonstrating the growth inhibition of S. aureus using $(PAR30/HA)_{24}$ or crosslinked $(PAR30/HA)_{24}$. $(PAR30/HA)_{24}$ was cross-linked using EDC/NHS with 0.5 M EDC and 0.1M NHS for 15 h at 4° C. Unreacted carboxyl groups were neutralized using ethanolamine. The normalized S. aureus growth (%) was measured in a supernatant after 24 h in contact with $(PAR30/HA)_{24}$ or crosslinked $(PAR30/HA)_{24}$ multilayer coatings. The growth of S. aureus is about 65% for crosslinked $(PAR30/HA)_{24}$ and less than 5% for $(PLL30/HA)_{24}$ thus showing that crosslinking reduces the biocidal activity of the coating.

To confirm the dependence of mobility on the bactericidal effect of the film, the inventors cross-linked the PAR30/HA multilayers using a standard EDC-NHS cross-linking method which creates a covalent link between amine groups of PAR and carboxylic groups of HA. The proportion of mobile chains measured by FRAP method decreases significantly from 88% for the non-crosslinked film to 20% for the cross-linked one (Data not shown). When the cross-linked film was brought in contact with *S. aureus*, only about 40% of inhibition of the bacterial growth was observed after 24 h of contact (FIGS. 9 and 10).

These results suggest that the percentage of mobile PAR chains in the multilayer is an important parameter controlling its bactericidal property of the film (FIG. 8).

Finally, using confocal microscopy, the inventors also investigated the structure of the film after 24 hours of contact with bacteria (Data not shown). For this purpose, films were constructed by incorporating fluorescently labelled PAR30 chains. It was found that after 24 hours of contact, the film is no longer homogeneous but that non-fluorescent areas appear. Because these areas have a smooth shape, they suggest a reorganization of the film. Such a behavior is not observed in the absence of bacteria where the films remain homogeneous. Such a reorganization could be consecutive to de decrease of the PAR chains in the film and suggest the following bactericidal mechanism: When bacteria come in contact with the multilayer, the negative bacteria membranes act as strong attractive surfaces for the PAR chains. Mobile PAR chains are thus soaked out of the film by the bacteria membranes and destabilize them. Chains of large molecular weight have a stronger membrane destabilization power than smaller molecular weight ones as it comes out from the MICs determined in solution. PAR10 chains are 10 times less active than PAR100 or PAR200 chains but PAR30 chains are only 2 times less active than PAR100 or PAR200 chains. Yet, in a film one can assume that the concentration of arginine monomers is fairly independent of the molecular weight of the PAR chains. Thus, the concentration of chains decreases when the molecular weight of the polyelectrolytes increases. For example the concentration PAR30 chains in the film should be 3 times higher than that of PAR100. In addition there are of the order of 90% of PAR10 chains that are mobile whereas only 70% of PAR100 chains are mobile. This leads to 4 times more PAR10 chains than PAR100 in the film. There could be other factors explaining the higher propensity of films PAR/HA films built with PAR30 to be strongly bactericidal but the chain mobility is without doubt an important one.

The inventors clearly demonstrate that the property of the coating is related to the length of the PAR polyelectrolyte chain. The concentration of the mobile PAR chains is a key-factor in the antimicrobial effectiveness and thus the films having 24 layers and being buildup with PAR containing 30 residues of arginine seem optimal for such bioactivity.

PAR containing 10 residues per chain seems not active in $(PAR/HA)_{24}$ films despite its high mobility in the films and its MIC which is close to that of PAR30. The inventors considered that this can be attributed to the film buildup which is about two times thinner with PAR10 compared to PAR30. After 24 bilayers, the amount of free PAR10 chains able to inhibit for 24 h bacterial growth could be too low.

Figure 13:
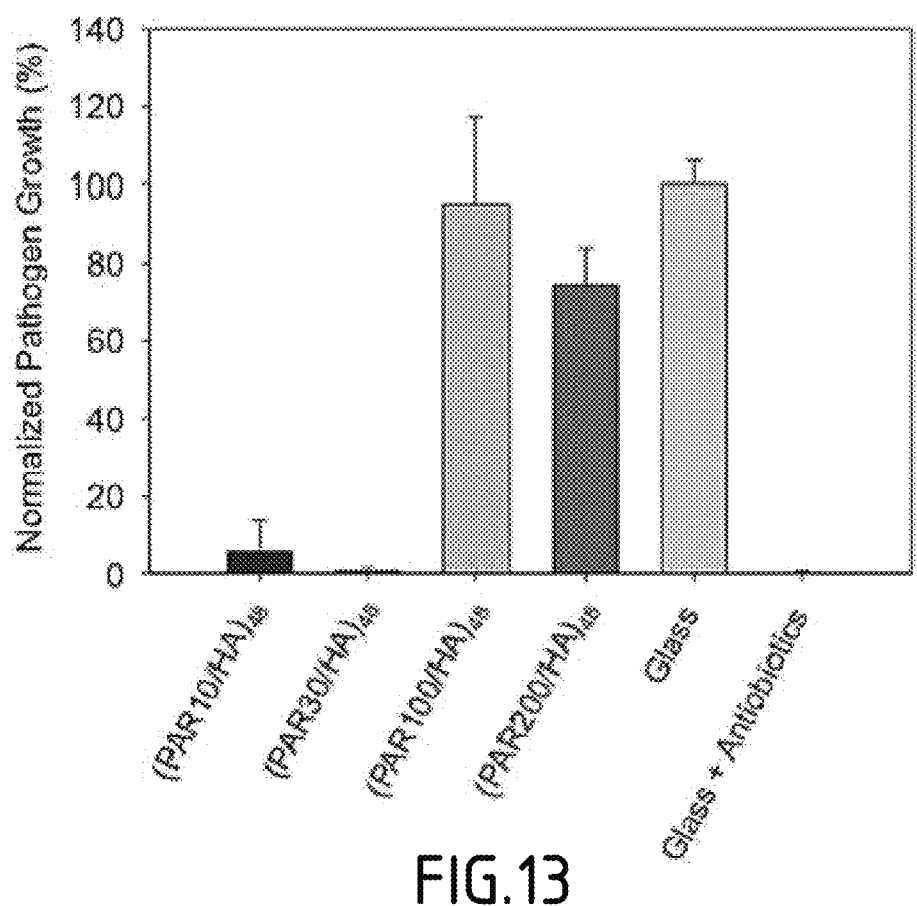
FIG. 13: Graph demonstrating the growth inhibition of S. aureus using different PAR coatings with 48 bi-layers. The normalized S. aureus growth (%) obtained in a supernatant after 24 h in contact with $(PAR/HA)_{48}$ multilayer coatings composed of poly-L-arginine with various number of residues is shown. Each value corresponds to the mean value of 3 experiments and error bars correspond to standard deviations. The growth of S. aureus is less than 10% for $(PAR10/HA)_{48}$ thus showing a strong growth inhibition of more than 90% for $(PAR10/HA)_{48}$, the growth of S. aureus is less than 2% for $(PAR30/HA)_{48}$ thus showing a strong growth inhibition of more than 98% for $(PAR30/HA)_{24}$, and the growth of S. aureus is about 95% for $(PAR100/HA)_{48}$ and about 75% for $(PAR200/HA)_{48}$.

To verify this hypothesis, the inventors performed therefore additional experiments with PAR10/HA films containing a higher number of bilayer (48 instead of 24) (FIG. 13). PAR10/HA films containing 48 bilayers become antimicrobial, however PAR100/HA or PAR200/HA remain inactive with 48 bilayers.

This indicates that a sufficient number of free PAR chains should be available to confer antimicrobial properties to the films. For PAR10 or PAR30, this number is reached with 48 or 24 bi-layers respectively.

The inventors consider that, concerning the mechanism of action of PAR30 (or PAR10 for thicker films), it should be related to diffusion of PAR30 or PAR10 chains out of the film enhanced by the attractive electrostatic interactions between the positively charged PAR and the negatively charged bacterial membrane. This interaction should occur as soon as the bacteria come in contact with the PAR/HA film. Time-lapse microscopy experiments have clearly shown that the bacteria are killed when they touch the PAR30/HA surface (data not shown). As PAR chains are mobile, they can diffuse and stick to the membrane. Then the mechanism should be closed to the mechanism of action of antimicrobial peptides, which are positively charged peptides that interact with bacterial membrane.

In order to investigate the biocompatibility of the PAR/HA coatings, the inventors seeded human primary fibroblasts from skin with medium that was in contact for 24 h with $(PAR30/HA)_{24}$ glass slides. After 24 h of seeding, no sign of toxicity was observed, the viability was equivalent to control conditions, i.e. glass surfaces (data not shown). This preliminary test demonstrates that the PAR released in the presence of medium in the supernatant shows no apparent sign of toxicity for the primary cells used. This is a positive point in the perspective of the application of PAR/HA films as coatings of implanted medical devices.

The inventors further investigated the biocidal activity of the coatings of the invention, in particular of $(PAR30/HA)_{24}$ coatings, over more than 24 hours. Therefore, a $(PAR30/HA)_{24}$ multilayer coating was put in contact with a fresh suspension of *S. aureus* after each 24 h and the $(PAR30/HA)_{24}$ shows after 24 and 48 h of incubation a total inhibition of bacteria and a bacterial growth that is strongly reduced (by 70%) after 72 h. This demonstrates the biocidal activity of the coatings of the invention over 3 days and three successive contaminations (FIG. 18).

To summarize, the inventors of the present invention have found that multilayer coatings comprising PAR, in particular PAR30 and PAR10, as polycation and HA as polyanion present a strong anti-microbial effect against *S. aureus*, *M. Luteus*, *E. coli* and *P. aeruginosa*. The inventors demonstrated in context of PAR30 coatings that this effect strikingly depends on the molecular weight of the polypeptide chains. This effect is explained by the concentration of mobile in the multilayers and their power to kill bacteria as a function of the molecular weight. This mechanism can be transferred to PAR10, because PAR30 as well as PAR30 both demonstrate high mobility.

However, under the conditions tested PAR10 films require more than 24 bilayers in order to be active. As demonstrated by the inventors since PAR10 and PAR30 have several capabilities in common the activity seems to depend on the amount of PAR10 or PAR30 present in the films and PAR10 biofilms require more PAR10 layers to obtain the same biocidal activity as PAR30 films.

These results open the route to new type of applications of polyelectrolyte multilayers, in particular of antibacterial multilayers, where the function can be tuned by the molecular weight of the polyelectrolytes.

The invention claimed is:

1. A polyelectrolyte coating having biocidal activity, comprising:
   (a) at least one polycationic layer consisting of at least one polyarginine consisting of n repetitive arginine units, wherein n is an integer comprised between 2 and 10 and wherein the individual polyarginine chains are mobile and/or diffuse within the polyelectrolyte coating, and
   (b) at least one polyanionic layer consisting of hyaluronic acid;
   wherein the polyelectrolyte coating comprises 40 to 200 polycationic layers and 40 to 200 polyanionic layers.

2. The polyelectrolyte coating according to claim 1, wherein said polyelectrolyte coating comprises 48 to 200 polycationic layers.

3. The polyelectrolyte coating according to claim 1, wherein said polyelectrolyte coating comprises 48 to 200 polyanionic layers.

4. The polyelectrolyte coating according to claim 1, wherein the number of the polycationic layers and the number of the polyanionic layers are the same or differ by one layer.

5. The polyelectrolyte coating according to claim 1, wherein said coating further comprises a pharmaceutical active drug.

6. The polyelectrolyte coating according to claim 1, wherein said coating is biocompatible.

7. A device comprising a polyelectrolyte coating having biocidal activity, wherein said polyelectrolyte coating comprises:
   (a) at least one polycationic layer consisting of at least one polyarginine consisting of n repetitive arginine units, wherein n is an integer comprised between 2 and 10 and wherein the individual polyarginine chains are mobile and/or diffuse within the polyelectrolyte coating, and
   (b) at least one polyanionic layer consisting of hyaluronic acid;
   wherein the polyelectrolyte coating comprises 40 to 200 polycationic layers and 40 to 200 polyanionic layers.

8. The device of claim 7, wherein the polyelectrolyte coating covers at least a portion of the surface of said device.

9. The device of claim 7, wherein said device is a medical device.

10. The device of claim 9, wherein said device is an implantable device.

11. The implantable device according to claim 10, wherein the implantable device is selected from the group comprising catheters, arteriovenous shunts, breast implants, cardiac and other monitors, cochlear implants, defibrillators, dental implants, maxillofacial implants, middle ear implants, neurostimulators, orthopedic devices, pacemaker and leads, penile implants, prosthetic devices, replacement joints, spinal implants, voice prosthesis, artificial hearts, contact lenses, fracture fixation device, infusion pumps, intracranial pressure device, intraocular lenses, intrauterine devices, joint prosthesis, mechanical heart valves, orthopedic devices, suture materials, urinary stents, vascular assist device, vascular grafts, vascular shunts and vascular stents, and artificial vessels of permanent or transient types.

12. A method for preparing a device comprising a polyelectrolyte coating having biocidal activity, the method comprising:
 (a) providing a device;
 (b1) depositing on the surface of said device
  (i) at least one polycationic layer consisting of at least one polyarginine consisting of n repetitive arginine units, wherein n is an integer comprised between 2 and 10, and then
  ii) at least one polyanionic layer consisting of hyaluronic acid, or
 (b2) depositing on the surface of said device ii) and then i) as defined above, and repeating b1) and/or b2) so that the polyelectrolyte coating comprises 40 to 200 polycationic layers and 40 to 200 polyanionic layers.

13. The method for preparing a device according to claim 12, further comprising at least one washing after i) and/or ii) of b1) or b2).

14. The method for preparing a device according to claim 13, further comprising at least one drying after i) and/or ii) of b1) or b2) and/or the at least one washing.

15. A method of preventing a bacterial infection in an individual undergoing an implantation of an implantable device comprising:
 i) providing an implantable device comprising a polyelectrolyte coating having biocidal activity, wherein said polyelectrolyte coating comprises:
  (a) at least one polycationic layer consisting of at least one polyarginine consisting of n repetitive arginine units, wherein n is an integer comprised between 2 and 10 and wherein the individual polyarginine chains are mobile and/or diffuse within the polyelectrolyte coating, and
  (b) at least one polyanionic layer consisting of hyaluronic acid,
  wherein the polyelectrolyte coating comprises 40 to 200 polycationic layers and 40 to 200 polyanionic layers, and
 ii) implanting said implantable device in the individual, wherein said implantable device prevents a bacterial infection.

16. The method of claim 15, wherein the bacterial infection is a nosocomial infection.

17. The polyelectrolyte coating according to claim 1, wherein said polyelectrolyte coating comprises 48 to 200 polycationic layers and 48 to 200 polyamomc layers.

18. The device of claim 7, wherein said device is a bandage.

* * * * *